(12) United States Patent
Njemanze

(10) Patent No.: US 11,487,891 B2
(45) Date of Patent: Nov. 1, 2022

(54) METHOD AND SYSTEM FOR MENTAL PERFORMANCE COMPUTING USING ARTIFICIAL INTELLIGENCE AND BLOCKCHAIN

(71) Applicant: Philip Chidi Njemanze, Owerri (NG)

(72) Inventor: Philip Chidi Njemanze, Owerri (NG)

( * ) Notice: Subject to any disclaimer, the term of this patent is extended or adjusted under 35 U.S.C. 154(b) by 0 days.

(21) Appl. No.: 17/070,553

(22) Filed: Oct. 14, 2020

(65) Prior Publication Data

US 2022/0114273 A1     Apr. 14, 2022

(51) Int. Cl.
*G06F 7/04* (2006.01)
*G06F 21/62* (2013.01)
(Continued)

(52) U.S. Cl.
CPC ........ *G06F 21/6218* (2013.01); *G06F 16/283* (2019.01)

(58) Field of Classification Search
CPC .... G06F 16/283; G06F 21/6218; G06F 21/64; H04L 9/50; G16H 10/60; G16H 40/67;
(Continued)

(56) References Cited

U.S. PATENT DOCUMENTS 6,390,979 B1 * 5/2002 Njemanze ................ A61B 8/06
600/438
6,468,219 B1 10/2002 Njemanze
(Continued)

OTHER PUBLICATIONS

Bagchi S. The Quantum Phenomena in Computational Model of Neuro-Cognition States: An Analytical Approach. NeuroQuantology, vol. 3, pp. 285-292, (2015).
(Continued)

*Primary Examiner* — Gary S Gracia

(57) ABSTRACT

The present invention generally relates to mental performance monitoring of brain activity that implements computing using blockchain and artificial intelligence technologies. Specifically, this invention relates to creating a blockchain from data obtained from a mental performance monitoring device that measures in real-time the mental activity and applying artificial intelligence machine-learning for pattern recognition of 'best performance' envelope to raise work efficiency, certify cognitive biometric status, detect cerebral microemboli, perform motor, sensory, facial, object and color processing tasks. The invention generally provides a mental status categorization that is implemented using a computer method for accessing, developing and maintaining a decentralized database through a peer-to-peer review network, to preserve the original state of 'best mental performance' envelope data inputs while applying artificial intelligence in a neural network model for pattern recognition of the changing mental states for use in cognitive biometrics, memory assessment, facial recognition, object recognition, language processing, odor recognition, color processing, psychomotor function, cognitive user preferences, task-difficulty, autonomy decision-making levels, and prediction of future actions. The system matches peer-to-peer clusters in a neural network of humans and human-robotic assembly for optimization of efficiency in task performance. The present invention could be applied to assist medical diagnosis through machine-learned models.

20 Claims, 10 Drawing Sheets

(51) Int. Cl.
*G06F 16/28* (2019.01)
*H04N 7/16* (2011.01)
(58) Field of Classification Search
CPC ........ G16H 50/20; G16H 50/70; G06N 20/00; G06N 3/08
See application file for complete search history.

(56) References Cited

U.S. PATENT DOCUMENTS

| | | | |
|---|---|---|---|
| 6,547,737 | B2 | 4/2003 | Njemanze |
| 6,663,571 | B1 | 12/2003 | Njemanze |
| 6,773,400 | B2 | 7/2004 | Njemanze |
| 7,942,820 | B2 | 5/2011 | Njemanze |
| 8,152,727 | B2 | 4/2012 | Njemanze |
| 9,608,829 | B2 | 3/2017 | Spanos et al. |
| 10,430,883 | B1* | 10/2019 | Bischoff ................ G06Q 20/14 |
| 10,817,950 | B1* | 10/2020 | Iqbal ........................ G07C 5/02 |
| 2018/0001184 | A1* | 1/2018 | Tran .................. G09B 19/0038 |
| 2019/0068367 | A1* | 2/2019 | Baughman .............. G06F 21/32 |
| 2019/0089701 | A1* | 3/2019 | Mercury ................. H04W 4/38 |
| 2019/0103192 | A1* | 4/2019 | Bent ...................... H04L 9/3239 |
| 2019/0286789 | A1* | 9/2019 | St Amant ............... G16B 40/00 |
| 2019/0287658 | A1* | 9/2019 | St Amant ............. H04L 9/0866 |
| 2019/0288837 | A1* | 9/2019 | St Amant ............. H04L 9/0894 |
| 2019/0288999 | A1* | 9/2019 | St Amant ............. G06F 3/0637 |
| 2019/0385711 | A1* | 12/2019 | Shriberg ................ G16H 50/20 |
| 2020/0045119 | A1* | 2/2020 | Weldemariam ....... H04L 67/535 |
| 2020/0103244 | A1* | 4/2020 | Celia ..................... A61B 5/6893 |
| 2020/0104966 | A1* | 4/2020 | Celia ........................ G07C 5/08 |
| 2020/0210978 | A1* | 7/2020 | Brown .................. H04L 9/3239 |
| 2020/0251213 | A1* | 8/2020 | Tran ....................... G06N 20/00 |
| 2020/0296480 | A1* | 9/2020 | Chappell, III ..... H04N 21/8545 |
| 2020/0342520 | A1* | 10/2020 | Pandey .................. G06Q 50/12 |
| 2020/0388359 | A1* | 12/2020 | Bhandari .............. H04L 67/306 |
| 2020/0393902 | A1* | 12/2020 | Mann ................. A61B 5/14553 |
| 2020/0405212 | A1* | 12/2020 | Chappell, III ......... H04H 60/33 |
| 2021/0049652 | A1* | 2/2021 | Brown ................. A61B 5/6807 |
| 2021/0110895 | A1* | 4/2021 | Shriberg ................ G06F 40/20 |
| 2021/0352134 | A1* | 11/2021 | Bjontegard ............. H04W 4/38 |
| 2022/0114273 | A1* | 4/2022 | Njemanze ............ G06F 16/283 |

OTHER PUBLICATIONS

Lueck CJ, Zeki S, Friston KJ, Deiber MP, Cope P, Cunningham VJ, Lammertsma AA, Kennard C, Frackowiak RS. The color centre in the cerebral cortex of man. Nature, vol. 340, pp. 386-389, (1989).
Njemanze, P.C. Gender-related asymmetric brain vasomotor response to color stimulation: a functional transcranial Doppler spectroscopy study. Exp. & Transl. Stroke Med., vol. 2, e21, (2010). Epub Dec. 2, 2010. https://doi.org/10.1186/2040-7378-2-21 PMCID: PMC3006356. PMID: 21118547.
Njemanze, P.C. Gender-related differences in physiologic color space: a functional transcranial Doppler (fTCD) study. Exp. & Transl. Stroke Med., vol. 3, pp. e1, (2011).
Njemanze, P. C. Kranz, M., Amend M., Hauser J., Wehrl H., and Brust P. Gender differences in cerebral metabolism for color processing in mice: A PET/MRI Study. PLoS One, vol. 12, pp. e0179919, (2017) https://doi.org/10.1371/journal.pone.0179919.
Njemanze P.C., Kranz, M., Brust, P. Fourier analysis of cerebral metabolism of glucose: gender differences in mechanisms of color processing in the ventral and dorsal streams in mice. Forecasting, vol. 1, pp. 121-142, (2019).
Njemanze P.C., Kranz, M., Brust, P. Gender Differences in Cerebral Metabolism Induced by Polarized Light in Mice Brain: A Quantum Coherence Model. Int J Nuclear Med Radioactive Subs, vol. 3(3): 000135, (2020).
Njemanze, P.C. Asymmetry in cerebral blood flow velocity with processing of facial images during head-down rest. Aviation Space and Environmental Medicine, vol. 75, pp. 800-805. (2004).
Njemanze P.C. Cerebral lateralization for facial processing: Gender-related cognitive styles determined using Fourier analysis of mean cerebral blood flow velocity in the middle cerebral arteries. Laterality, vol. 12, pp. 31-49, (2007).
Njemanze P.C. Cerebral lateralization for motor tasks in simulated microgravity. A transcranial Doppler technique for astronauts. Journal of Gravitational Physiology, vol. 9, pp. 33-34, (2002).
Stroobant, N., and Vingerhoets G. Transcranial Doppler ultrasonography monitoring of cerebral hemodynamics during performance of cognitive tasks. A review. Neuropsychological Review, vol. 10, pp. 213-231 (2000).
Njemanze, P.C. Cerebral lateralisation in random letter task in the visual modality: A transcranial Doppler study. Brain and Language, vol. 53 , pp. 315-325, (1996).
Njemanze, P.C. Cerebrovascular dysautoregulation syndrome complex—brain hypoperfusion precedes hypotension and cardiac asystole. Jpn. Circ. J. vol. 58, pp. 293-297, (1994).
Njemanze P.C., Antol P.J., Lundgren C.E.G. Perfusion of the visual cortex during pressure breathing at different high-G stress profiles. Aviat. Space Environ. Med. vol. 64, pp. 396-400, (1993a).
Njemanze P.C. Cerebral circulation dysfunction and hemodynamic abnormalities in syncope during upright tilt test. Can. J. Cardiol. vol. 9, pp. 238-242, (1993b).
Njemanze P.C. Critical limits of pressure-flow relation in the human brain. Stroke, vol. 23, pp. 1743-1747, (1992).
Njemanze P.C. Transcranial Doppler evaluation of syncope: An application in aerospace physiology. Aviat. Space Environ. Med. vol. 62, pp. 569-572, (1991a).
Njemanze, P.C. Cerebral lateralisation in linguistic and nonlinguistic perception: Analysis of cognitive styles in the auditory modality. Brain and Language, vol. 41, pp. 367-380, (1991b).

* cited by examiner

METHOD AND SYSTEM FOR MENTAL PERFORMANCE COMPUTING USING ARTIFICIAL INTELLIGENCE AND BLOCKCHAIN

CROSS-REFERENCE TO RELATED APPLICATION

U.S. Patent Documents

| | Document Number | Date | Name | Classification | Cited by |
|---|---|---|---|---|---|
| 1. | U.S. Pat. No. 6,390,979B1 | May 2002 | Njemanze, Philip C. | 600/438 | Inventor |
| 2. | U.S. Pat. No. 6,468,219B1 | October 2002 | Njemanze, Philip C. | 600/454 | Inventor |
| 3. | U.S. Pat. No. 6,547,737B2 | April 2003 | Njemanze, Philip C. | 600/454 | Inventor |
| 4. | U.S. Pat. No. 6,663,571 | December 2003 | Njemanze Philip C. | 600/504 | Inventor |
| 5. | U.S. Pat. No. 6,773,400 | July 2004 | Njemanze Philip C. | 600/454 | Inventor |
| 6. | U.S. Pat. No. 7,942,820 | May 2011 | Njemanze Philip C. | 600/441 | Inventor |
| 7. | U.S. Pat. No. 8,152,727 | April 2012 | Njemanze Philip C. | 600/454 | Inventor |
| 8. | U.S. Pat. No. 9,608,829 | March 2017 | Spanos Nikolaos et al. | G06F 21/64 | Inventor |

OTHER PUBLICATIONS

Bagchi S. The Quantum Phenomena in Computational Model of Neuro-Cognition States: An Analytical Approach. *NeuroQuantology*, vol. 3, pp. 285-292, (2015).

Lueck C J, Zeki S, Friston K J, Deiber M P, Cope P, Cunningham V J, Lammertsma A A, Kennard C, Frackowiak R S. The color centre in the cerebral cortex of man. *Nature*, vol. 340, pp. 386-389, (1989).

Njemanze, P. C. Gender-related asymmetric brain vasomotor response to color stimulation: a functional transcranial Doppler spectroscopy study. *Exp. & Transl. Stroke Med.*, vol. 2, e21, (2010). Epub 2010/12/02. https://doi.org/10.1186/2040-7378-2-21 PMCID: PMC3006356. PMID: 21118547.

Njemanze, P. C. Gender-related differences in physiologic color space: a functional transcranial Doppler (fTCD) study. *Exp. & Transl. Stroke Med.*, vol. 3, pp. e1, (2011).

Njemanze, P. C. Kranz, M., Amend M., Hauser J., Wehrl H., and Brust P. Gender differences in cerebral metabolism for color processing in mice: A PET/MRI Study. *PLoS One*, vol. 12, pp. e0179919, (2017) https://doi.org/10.1371/journal.pone.0179919.

Njemanze P. C., Kranz, M., Brust, P. Fourier analysis of cerebral metabolism of glucose: gender differences in mechanisms of color processing in the ventral and dorsal streams in mice. *Forecasting*, vol. 1, pp. 121-142, (2019).

Njemanze P. C., Kranz, M., Brust, P. Gender Differences in Cerebral Metabolism Induced by Polarized Light in Mice Brain: A Quantum Coherence Model. *Int J Nuclear Med Radioactive Subs*, vol 3(3): 000135, (2020).

Njemanze, P. C. Asymmetry in cerebral blood flow velocity with processing of facial images during head-down rest. *Aviation Space and Environmental Medicine*, vol. 75, pp. 800-805. (2004).

Njemanze P. C. Cerebral lateralization for facial processing: Gender-related cognitive styles determined using Fourier analysis of mean cerebral blood flow velocity in the middle cerebral arteries. *Laterality*, vol. 12, pp. 31-49, (2007).

Njemanze P. C. Cerebral lateralization for motor tasks in simulated microgravity. A transcranial Doppler technique for astronauts. *Journal of Gravitational Physiology*, vol. 9, pp. 33-34, (2002).

Stroobant, N., and Vingerhoets G. Transcranial Doppler ultrasonography monitoring of cerebral hemodynamics during performance of cognitive tasks. A review. *Neuropsychological Review*, vol. 10, pp. 213-231 (2000).

Njemanze, P. C. Cerebral lateralisation in random letter task in the visual modality: A transcranial Doppler study. *Brain and Language*, vol. 53, pp. 315-325, (1996).

Njemanze, P. C. Cerebrovascular dysautoregulation syndrome complex—brain hypoperfusion precedes hypotension and cardiac asystole. *Jpn. Circ. J.* vol. 58, pp. 293-297, (1994).

Njemanze P. C., Antol P. J., Lundgren C. E. G. Perfusion of the visual cortex during pressure breathing at different high-G stress profiles. *Aviat. Space Environ. Med.* vol. 64, pp. 396-400, (1993a).

Njemanze P. C. Cerebral circulation dysfunction and hemodynamic abnormalities in syncope during upright tilt test. *Can. J. Cardiol.* vol. 9, pp. 238-242, (1993b).

Njemanze P. C. Critical limits of pressure-flow relation in the human brain. *Stroke*, vol. 23, pp. 1743-1747, (1992).

Njemanze P. C. Transcranial Doppler evaluation of syncope: An application in aerospace physiology. *Aviat. Space Environ. Med.* vol. 62, pp. 569-572, (1991a).

Njemanze, P. C. Cerebral lateralisation in linguistic and nonlinguistic perception: Analysis of cognitive styles in the auditory modality. *Brain and Language*, vol. 41, pp. 367-380, (1991b).

STATEMENT REGARDING FEDERALLY SPONSORED RESEARCH OR DEVELOPMENT

Not Applicable

REFERENCE TO MICROFICHE APPENDIX

Not Applicable

FIELD OF THE INVENTION

The present invention generally relates to mental performance monitoring of brain activity that implements computing using blockchain and artificial intelligence technologies. Specifically, this invention relates to creating a blockchain from data obtained from a mental performance monitoring device which measures in real-time the mental activity and applying artificial intelligence machine-learning for pattern recognition of 'best performance' envelope to raise work efficiency and certify cognitive biometric status. The invention generally provides a mental status categorization that is implemented using a computer method for accessing, developing and maintaining a decentralized database through a peer-to-peer review network, to preserve the original state of 'best mental performance' envelope data inputs while applying artificial intelligence in a neural network model for pattern recognition of the changing mental states associated with cognitive biometrics, memory, facial recognition, object recognition, language processing, odor recognition, psychomotor function, sleep, cognitive user preferences, task-difficulty, autonomy decision-making levels, cerebral microemboli detection and prediction of future actions. The system matches peer-to-peer clusters in a neural network of humans and human-robotic assembly for optimization of efficiency in task performance, and assessing a reward system.

BACKGROUND OF THE INVENTION

Artificial Intelligence (AI) and blockchain technologies are rapidly emerging technologies with promise to provide solutions to several areas of human endeavor. AI techniques are collectively known as machine learning. Machine learning is simply that a machine learns a task without being programmed with explicit instructions. The algorithms of the machine are designed with the ability to discover relationships within the provided data. On the other hand, blockchain is a new filing system for digital information, which encodes data in an encrypted, distributed ledger format. In other words, data held in blockchains are highly secure, because of cryptography used in the filing system. The blockchains are ideal for storing the highly sensitive personal data that are collected with the present invention which integrates the AI technologies. The obtained encrypted data are distributed across many different computers. This enables the creation of tamper-proof, highly robust databases which can be read and updated only by those with permission. On the other hand, blockchain technology is most widely associated with cryptocurrency, but is now gaining use in several applications in different areas. Cryptocurrency just like ordinary money is implemented as a reward system for valid mental performance task. However, simply put, a blockchain creates a history of data deposits, messages, or transactions in a series of blocks where each block contains a mathematical summary, called a hash, of the previous block. This creates a chain where any changes made to a block will change that block's hash, which must be recomputed and stored in the next block. This will change the hash of the next block, which must be recomputed and so on going down to the end of the chain. The state-of-the art impose rules which require the value of the hash to be below a certain threshold value. Furthermore, the hash is based on a special type of mathematical function that is not reversible; you cannot predict what input can be used to produce the desired output. To find a valid hash, a changeable value in the block is repeatedly adjusted and recalculating the hash until it meets the validity requirements. The freely changeable value is called the nonce. The value of the hash is not predictable, thus increases the difficulty of finding a nonce that produces a valid hash of the block.

The recording of mental state performance data raises serious privacy and ethical issues. It involves huge amount of data recorded on a datapoint-by-datapoint basis in real-time, in a blockchain, which requires large computer processing power. The machine learning-powered mining algorithm is deployed as a hashing algorithm used to mine blocks. In the present invention, the two technologies, blockchain and AI, which are ground-breaking technological trends in their own respective rights, but now innovatively combined with the potential to become even more revolutionary. Both technologies have been implemented in the present invention to enhance the capabilities of secure storage and analysis, while also offering opportunities for better oversight and accountability.

Mental performance could be monitored using brain electrical potentials, cerebral blood flow, cerebral blood flow velocity or brain metabolism. To illustrate the concept, we would apply the use of measurements cerebral blood flow velocity, just as an example, which should not limit its use to only this parameter. It has been shown that, mental performance implicating higher order intelligence could be determined using non-invasive transcranial Doppler ultrasound measurement of mean cerebral blood flow velocity (MCBFV) in the right and left middle cerebral arteries in the brain in male and female subjects (Stroobant & Vingerhoets, 2000). The results demonstrated that, for successful resolution of Raven Progressive Matrices (RPM) tasks, females used a left hemisphere strategy while males used the right hemisphere (Njemanze, 2005). Similarly, facial processing was associated with the right hemisphere in men but in the left hemisphere in women (Njemanze, 2007). Color processing was implemented in the right hemisphere in men but in the left hemisphere in women (Njemanze, 2010, 2011). On the other hand, color processing was detected in the right hemisphere in female mice but in the left hemisphere in male mice (Njemanze et al., 2017, 2019). Studies in humans suggested that, general intelligence, facial processing and color processing are associated with neural network systems within the right hemisphere in men and in the left hemisphere in women, that are accessible to a variety of cognitive processes (Njemanze, 2005, 2007, 2010, 2011). There were detectable changes in cerebral blood flow velocity associated with motor and facial tasks both in normal earth 1G conditions and in simulated microgravity (Njemanze, 2002, 2004). Similarly, studies of cerebral metabolism during stimulation with colors and polarized light have revealed novel findings, which demonstrated that, light stimulation evoked wavelength-differencing effects in the visual cortex of male mice but frequency-differencing effects in the visual cortex of female mice (Njemanze et al., 2020). Furthermore, quantum superposition effect of coherence was observed in the brain of female mice, while the effect observed in male mice was classical wave superposition, leading to the preposition that, female mice could be used to study neural networks that could be implemented in quantum computer models (Njemanze et al., 2020).

Furthermore, cerebral blood flow velocity is a useful predictor of levels of consciousness (Njemanze, 1992, 1992). In conditions of normal earth gravity (1G) and in hypergravity conditions, that could result in gravitational loss of consciousness (GLOC) such as in high-performance avionic systems, cerebral blood flow velocity showed early indication of diminution before peripheral light loss (PLL) and GLOC (Njemanze, 1993a). The U.S. Pat. No. 5,121,744, 1992 to Njemanze P. C. describes a transcranial Doppler device with probe integrated into a helmet to detect changes in MCBFV during impending GLOC, with G-suit to initiate countermeasures. The brain hypoperfusion during impending loss of consciousness preceded hypotension and cardiac asystole (Njemanze, 1994). The latter suggests the tight relation between levels of MCBFV and human consciousness (Njemanze, 1992, 1993a, 1993b). Furthermore, higher-order brain functions could be monitored using measurements of MCBFV. It has been demonstrated that, there are differences in cerebral blood flow velocity in the right and left middle cerebral arteries during higher cognitive functions of language processing (Njemanze, 1991b, 1996), general intelligence (Njemanze, 2005), facial processing (Njemanze, 2007), color processing in humans (Njemanze, 2010, 2011) and animals (Njemanze, 2017, 2019, 2020). It therefore follows that, measurements of cerebral blood flow velocity and its lateral differences, could be used as index for mental state-of-being. The present invention securely stores MCBFV in blockchain, and analyzes the data using AI system to determine the mental state-of-being of a person. Various computational models (Bagchi, 2015) could be applied to mental performance to determine the mental state-of-being using machine-learning AI technologies.

The present invention seeks to utilize the combined capabilities of AI for pattern recognition and the blockchain for data encryption of mental performance data and determination of mental state-of-being of a human subject interfaced with a computer or computer network. The present invention would solve several problems in the areas of cybersecurity, cognitive biometrics, defense, self-driving cars, increased work efficiency, enhanced peer-to-peer networking, mental prosthesis, human-robotic interface, video gaming, intelligent computer operating systems, digital currency reward system, artificial intelligent quantum computer models, and improved air-safety measures.

The present invention could help overcome pilot error in controlled flight into terrain (CFIT) caused by loss of situational awareness. The present invention stores best performance envelope and real-time changes in mental performance of the pilot in blockchain and implements AI technologies for pattern recognition of the mental status and uses it to regulate autonomy-decision-making level between the pilot and autopilot on detection of cerebral blood flow changes suggestive of loss of situational awareness in the pilot.

In our present era and going into the future, network security would be of utmost importance. In the present era of cyberterrorism, we are in a crisis situation whereby the gains of speed and ease of use of internet technology is being eroded by the danger of unwarranted use. There is need to improve security both for personal identification and cooperate identity. The introduction of use of finger-printing and facial recognition may have added some level of security, but it is grossly inadequate in many areas of application especially with regard to terrorism. Take for example, a military pilot of F-18 plane may be 'radicalized' and wants to fly his jet with bombs into the 'White House' with the intent to commit an act of terror. The personal identification, finger print and facial recognition will give him a pass to fly the F-18 jet. However, the present invention would detect the mental state-of-being of the pilot for cognitive-biometrics and determine that he is not in his best performance status and decline him access to fly the F-18 plane. Similarly, in both military and civil aviation, the present invention can determine poor mental state of alertness, sleep, emotional stress and pass onto the auto-pilot the control the aircraft during periods of poor mental status.

As the era of self-driving cars is fast approaching, it may be necessary to determine when the driver can override the auto-driver. For example, a self-driving car using AL, will perform well in traffic under normal conditions. However, in a situation where on the way chaos ensues due to a bomb explosion or natural disaster, there would be need for the human driver to either take over or offer advice in a shared control setting with the self-driving car. On the other hand, the auto-driver of the self driving car could detect a tendency towards sleep pattern or effects of alcohol in the human driver, and takes over control of the car to avert accidents. The shared control settings would allow the self-driving car to use the perceptive inputs of the human person to navigate out of serious dangers. Therefore, the self-driving car would need a continuing interrogation of the mental state-of-being the human driver-designate to make sure it is receiving directives of a person in good mental state. The present invention would allow the self-driving car to alternate autonomy-decision making with the human-driver at critical moments.

Most often, employers are faced with the task of maximizing work efficiency by pairing groups of talented employees. At present, this is done by empirical evidence collected from previous test scores which does not take into consideration the current real-time mental performance. It is desirable to have a mental state-of-being measure that could be determined in real-time and use it to cluster groups that are similar, different or complimentary in mental performance. The present invention seeks to provide a solution to determining the mental state-of-being of human persons in a manner that securely stores the data in a blockchain, and then applies AI methods for cluster analysis to find groups of observations that are similar to one another, and could complement each other. The similarity/difference is captured by the metric called distance. The AI application could be used to select a group of persons with mental performance skills needed for a particular task. For example, a mission may require a pilot with high object recognition skills, while another with better dexterity-motor skills and yet another with greater level of general intelligence. A combination of persons with complimentary cognitive skills into a group could assure mission accomplishment.

The human nose has the capacity to discern over 1 trillion scents. In some cases, criminal investigators and perfume designers are interested in a particular odor effect on the mental state-of-being of a human being or animal such as a dog. The U.S. Pat. No. 6,663,571 to Njemanze P. C. describes a transcranial Doppler ultrasound device for odor evaluation. The present invention applies blockchain to securely store the data and AI technologies for pattern recognition of the effects of different odors acquired with data such as that from the '571' patent, and to mine the data. The AI technologies apply statistical methods to detect the trend of changes in mental performance and their relationship with odors in the large database of varying effects.

Designers of cloths, decorators and artists creatively use colors in their different designs, but the state-of-the art approach is based on empirical evidence. The human eye can distinguish about 10 million different colors. Njemanze and others, have demonstrated that colors evoke measurable changes in MCBFV in the brain in humans (Njemanze, 1992, 2010, 2011) and mice (Njemanze, et al. 2017, 2019, 2020). The U.S. Pat. No. 8,152,727 to Njemanze P. C. describes a method for assessment of color processing mechanism in the human brain for diagnosis and treatment. Yet another U.S. Pat. No. 7,942,820 to Njemanze P. C. describes a method and system for evaluation of hemodynamic model in depression for diagnosis and treatment. The present invention implements blockchain to securely store the MCBFV data and applies AI technologies to pattern recognition of color processing in patients for diagnosis and treatment brain diseases and disorders such as depression, Alzheimer's disease and other degenerative brain diseases.

Sometimes, the task may require analytical and strategic planning. It is known that women use left hemisphere processing for general intelligence with high analytic capabilities, while men use the right hemisphere with strategic planning capabilities (Njemanze, 2005). A peer-to-peer network pairing with complimentary capabilities based on patterns of variations using AI could be performed. Similarly, dating and match-making services could use the new invention to find male/female partners that are complimentary based on cognitive styles (Njemanze, 2007).

The U.S. Pat. No. 6,468,219 to Njemanze P. C. demonstrates a method of using cerebral blood flow velocity measurements indexed by transcranial Doppler ultrasound implanted on the temporal bones to monitor microembolic signals discharged into the brain, said signals are used to trigger injection of anticoagulant in a pump implanted under the skin, to prevent a stroke in patients with vascular lesions, vascular grafts, blood coagulation abnormalities, atrial fibrillation, etc. The '219' patent requires transmission of the signal to a remote physician via mobile phone technology to evaluate the microembolic signal to give consent before injection of the anticoagulant. This leads to loss of valuable time that could be avoided to save lives. The present invention could be applied to prevent stroke and heart attacks in patients by detecting microembolic signals using implantable transcranial Doppler ultrasound as described in the '219' patent and applying blockchain to securely store the data and AI technologies to perform pattern recognition of the microembolic signals and automatically triggering the implanted pump to inject anticoagulant into the patient, saving valuable time for prevention of strokes and heart hearts.

It is known that medical diagnostic accuracy could be as low as 60% when one expert is involved in the decision-making. Medical diagnostic accuracy could be significantly improved through machine-learning approaches. Prior art includes medical expert systems like Mycin for infectious diseases, Internist-1, QMR and DXplain for general medicine. These medical expert systems generally include a knowledge base, which encapsulates the evidence-based medical knowledge that is curated by medical experts, and a rule-based inference engine devised by the expert, which operates on the knowledge base to provide a differential diagnosis. The present invention uses an innovative approach, first, to determine the mental performance of the medical examiner at the time of the examination of the patient to ascertain the reliability of the diagnosis and then consulting with the medical expert system to evaluate more options of differential diagnosis. The AI machine-learning system adapts its methodology and rule-based heuristics from the patterns observed in the medical examiner.

Njemanze (2005) demonstrated that for a successful resolution of general intelligence tasks such as Raven Progressive Matrices (RPM), females used a left hemisphere strategy while males used the right hemisphere. This implies that general intelligence is associated with neural systems within one hemisphere that are accessible to a variety of cognitive processes. The present invention utilizes some basic scientific concepts demonstrated by research and innovatively applied them to use of blockchain, AI and cognitive biometrics, as demonstrated in the illustrations below. The application of transcranial Doppler ultrasound to recording of mental performance has been described in the teachings in U.S. Pat. No. 6,390,979, (2002) and in the cited literature (Njemanze, 2005). Parametric measures in form of brain electrical signals, cerebral blood flow and brain metabolism have been developed and could be applied in a similar manner.

The block hash could calculate the hemispheric advantage using laterality index (LI) expressed as:

$$LI_o = (Right\ MCBFV_o - Left\ MCBFV_o / Right\ MCBFV_o + Left\ MCBFV_0) * 100.$$

The hemisphere advantage or relative $LI^1$ denotes the relationship between a block and the previous block was given by $$LI^1_1 = LI_1 - LI_0$$

Positive LI suggests either a right lateralization or hemisphere advantage, while negative LI shows left lateralization. Zero LI may suggest no change from baseline or equal bilateral activation. The changes in laterality index during mental performance using RPM tasks is shown in FIG. 1. In male subjects, the LI increases to higher positive values when the response is correct, showing a right hemisphere advantage, but reduces when the response is wrong with a tendency towards left hemisphere involvement. On the other hand, in female subjects, the LI decreases to lower negative values when the response is correct, showing a left hemisphere advantage, but increases when the response is wrong with a tendency towards right hemisphere involvement. It therefore follows that, a right hemisphere increased neuronal activity is associated with intelligent solutions in male subjects, while in female subjects intelligent solutions were associated with the left hemisphere. Involvement of the contralateral hemisphere indicated comprise in the effort to search for the correct answers. The present invention innovatively applies blockchain, AI and cognitive biometric technologies to mental performance monitoring using data collected with transcranial Doppler ultrasound measured MCBFV in the right and left MCAs during mental performance. The present invention could also apply other indicators of mental performance using brain electrical potentials, cerebral blood flow and brain metabolism to make similar calculations.

The present invention could apply AI and blockchain technologies for programmed neural network machine-learning and integration of mental prosthesis used in training and physical rehabilitation of psychomotor functions in patients with limb prosthesis or in conditions of limb paralysis after stroke. Applying trained AI pattern recognition according to the teachings of this invention, the movements of a trainer evokes changes in brain activity in motor areas which could be telemetrically transmitted for brain-brain connectivity to replicate similar motor activity in the patient with an implanted nerve stimulation device in the analogous (corresponding in function) area of the brain or in homologous area of the contralateral hemisphere to enhance neuroplasticity. This means that analogous areas of the brain in the trainer and patient could be telemetrically linked, such that movement (kinesis) in the trainer elicits stimulation of the same area in the patient's brain. The latter is known as telekinesis physical therapy. The intensity of neuronal stimulation for movement by the patient is dependent on the neuronal activity generated in the brain of the trainer. The parametric measures used to detect movement in the brain include but not limited to somatosensory evoked potentials, spontaneous electrical potentials, cerebral blood flow, cerebral blood flow velocity, and brain metabolism. The present invention uses blockchain and AI technologies to facilitate physical therapy by telekinesis. The AI technology system of the present invention is capable of machine-learning after the training process and could replicate the physical therapy by telekinesis on its own without the trainer.

One embodiment of the present invention teaches that, the AI pattern recognition of mental performance could be used for telemetric control of robotic systems. The state-of-the-act control of robotic systems is based on hand movement of the operator that moves the robotic arm remotely or by programmed control. The reliance on dexterity (manual use of limbs) of the operator has several drawbacks when operating remotely with the robotic arm. To eliminate these problems such as depth-perception, some have applied three-dimensional viewing in virtual reality to add higher degree of precision. The present invention teaches that, the task could be performed mentally through human-robotic sensory interface for telekinesis of psychomotor control of robotic arm. In other words, the operator thinks and moves with the robotic arms as if it were his/her own arms. The patterns of mental performance changes during programmed movement by the operator is translated by the AI system for telemetric control of the robotic arm. The operator uses the internalized mental imagination to move the robotic arm. The latter new AI concept could be described as human brain-telerobotic 'theory of mind', where the human through introspection has direct access for 'mind'-control of the robot in a manner analogous to self activity. The same concept of human brain-telerobotic 'theory of mind' could be a new approach for mind-control telerobotic surgery, that is, surgery using the human mind to control robotic dexterity during surgical operation. The latter could be crucial in many day-to-day life situations. In a situation where a surgeon suffers a skiing accident and breaks an arm bone, it could take several months to heal or could result in permanent physical deficits. Similarly, experienced old surgeons who are sound in mind could continue to operate and teach new younger surgeons even when they are physically frail. The surgeon could continue to perform lifesaving operations despite physical frailty, using the AI technology of mental performance described in the present invention, which applies the concept of 'theory of mind' control telerobotic surgery by the AI Surgeon Expert System hereby described for the first time.

One embodiment of the present invention could be applied for medical diagnostic expert systems based on monitoring mental performance. Medical diagnosis is based on observation of symptoms and signs. The present invention applies blockchain to store the information of the expert knowledge-base and that of the patient and the machine-learning algorithms for training the AI expert system.

Another use of the present invention is in the gaming industry to develop video game consoles. The computer games on platforms such as Sony-Playstation, Nintendo-Switch. Microsoft-Xbox, and others, could use the present invention to assess the level of mental performance of the gamer and upgrade or downgrade the level of difficulty posed by the game tasks according to the mental state-of-being of the gamer. Since most gamers are children below 15 years of age with developing brains, mental stress posed by a game could be deleterious to their overall mental development. It is important for government regulators to have metric systems to prohibit high levels of mental stress measurable in real-time during the video game. It is therefore desirable for all games to comply with the restriction to prevent mental stress in a gamer. Prior act in the teachings of U.S. Pat. No. 6,390,979, describes the application of transcranial Doppler ultrasound to recording of mental performance. However, the state-of-the-art has no measurable real-time monitoring of mental performance during video games. The present invention would monitor patterns of mental performance in a gamer in real-time during the video game and could apply AI to differentiate patterns associated with mental stress from those not associated with stress as encoded in a blockchain on a peer-to-peer network. The present invention could perform a network wide assessment of the hash data and apply AI technologies to mine data for assessment of overall mental stress levels. When the present invention performs a real-time determination of mental stress patterns the device could either downgrade the level of difficulty of the game, exclude a particular gamer from the network or even terminate the game entirely for a rest period for the gamers.

In another embodiment, the present invention uses the concept of 'theory of mind' to play the 'Mind Game'. The present state-of-the act uses dexterity for user control interface, for all game consoles. However, the present invention implements an innovative concept of 'Mind Game Telekinesis' as the user control interface for video games and other games like Chess and Drafts. The gamer moves the control interface or machinery using the mind. The new generation 'Telekinetic Video Games' works by the gamer intending a movement which changes the brain activity in the sensorimotor area of the brain, detected by the brain activity sensor attached to the present invention, which in turn causes activation of movement through the game console or robotic arm to effect the game activity.

In yet another embodiment, a person could perform psychic control of computer settings, typing text, perform speech, and motor activity using a 'Telepsychic Computer'. The telepsychic computer by the person intending to make a change, for example, of the color background, and 'thinking blue' would activate the center for blue color in the brain (Njemanze, 2010, 2011. 2017, 2019, 2020), that changes the brain activity, which could be indexed by changes in brain electrical potentials, cerebral blood flow, cerebral metabolism, or cerebral blood flow velocity, at the 'color center' in the brain (Lueck et. al. 1989). The present invention in turn causes the game console to effect a background color change. Similarly, telepsychic control of computers could be used for writing text and speech. The present invention effects telepsychic control to aid the physically challenged. The telepsychic control telemetrically connects with the physically challenged to a robotic assistant in a manner where the person exerts 'Mind Control' of the robot. At a geriatric home, a physically challenged person who cannot speak could use only the mental activity to direct the nurse assistant-robot to get a cup of water from the fridge. The telepsychic robotic nurse assistant would be crucial in nursing homes for the aged as human care-givers become rare and more expensive.

A person working on a computer to complete a particular task may at some point lack the necessary information to proceed with the task. In such a situation the person might start seeking information to help him/her to accomplish the task. However, the problem is usually that the person is unaware of websites on the Internet where such information could be obtained. In the present state-of-the-art, search engines may use words to present options to the person. The present invention solves this problem by first determining that the mental state-of-being of the person shows some compromise and the need arises to provide help, which triggers the operating systems of personal computer, workstation and/or internet to utilize the search engine, guided by keywords from the task to provide online information needed to complete the task. These suggestions could vary such as templates of letters, literature citations, dictionary, online consultancy etc. The real-time continuing assessment of the person determines when the mental state-of-being has returned to normal state and the system stops suggesting solutions. The tasks may be as simple as writing a good job application to complex issues as coding new AI software.

The problem in jobs demanding high mental stress such as air-traffic control requires that the controller be in a good mental state-of-being at the peak of work time. It is desirable to determine the real-time mental state-of-being of the air-traffic controllers in a peer-to-peer network such that, the autonomy decision-making for direction of traffic could be alternated between the controller and his/her supervisor at critical periods of performance decrement. The present invention determines mental performance patterns using blockchain and AI system that is continually compared to the real-time mental performance, and if decrement is detected the autonomy-decision making is passed on to the supervisor.

The monitoring of mental performance is a suitable case for implementation of blockchain. The first step in building the blockchain, would assure it provides immutable storage of the data, digital 'mental' signatures and encryption. The data could be managed by the AI system to provide the most efficient and intelligent options of the hybrid from human-machine interface solutions that offer the smartest solutions to a given task. In the second step, it utilizes at least one of the options such as proof-of-work to provide a consensus mechanism. The third step entails using a suitable platform of which there are many free open source options (Big-ChainDB, Chain Core, Ethereum, HydraChain etc.) depending on the consensus mechanism chosen. The fourth step involves the designing of the nodes, which could be private, public or hybrid. Some could be permissioned like those for military applications, and others could be open as permission-less. The fifth step would require design of the blockchain instance involving planned configuration for permissions, key formats, block signatures, hand-shaking etc. The sixth step involves building the application program interface (API), to specify how the software components should interact. The seventh step would implement design for the admin and user interface, which is the front end and programming languages (e.g. HTML5, Javascript, Python, Ruby, Golang etc.). External databases (e.g. MySQL, MongoDB) and servers (web servers, FTP servers and mail servers) could be chosen. The blockchain solution could be integrated with the Artificial Intelligence, and Cognitive Biometrics systems for data mining.

In yet another embodiment of the present invention involves monitoring of mental performance using blockchain and AL, and uses a rewarding system including a form of digital currency when the AI system indicates a valid contribution, the said task could be a game, sports, office assignment or stock market trading.

Another advantage for use of the blockchain for mental performance monitoring in a distributed network is the increased security. This means a large number of users with access to the network working together on a task with their mental performance continually monitored in real-time would be adding the blocks to the blockchain that correlates with their actual valid contribution towards the solution of the task. The AI systems determines valid contributions and adds the blocks to the end of the chain by finding a nonce that produces a valid hash for a given block of data. When two blocks are found that both claim to reference the same previous block, a fork in the chain is created. In seeking solution to the task, some users in the network may attempt to find the next block on one end of the fork while other users will work from the other end of the fork. On the long run, one of the forks will grow longer than the other in length, and the longest chain is accepted by consensus as the valid chain. This would correlate to the correct path to the solution of the problem. In the present state-of-art, anyone who attempts to change a block must not only re-find a valid hash for each subsequent block, but must do it faster than everyone else working on the currently accepted chain. Thus, after a certain number of blocks have been chained onto a particular block, it becomes prohibitively costly to try to change that block. However, there are rules or protocols governing the blockchain and its data, which accommodate blockchain forks allowing each side of the fork to store valid data that could be used by the AI system to find alternative path to the solution of the problem. These and other major features and advantages of the present invention will be explained and will become obvious to one skilled in the art through the summary of the invention that follows.

SUMMARY OF THE INVENTION

Accordingly, it is an object of the present invention to provide a system and method that collects mental performance data based on brain electrical activity, brain metabolism, brain cerebral blood flow, cerebral blood flow velocity or any other indicator of mental performance in a blockchain database and to mine the data using artificial intelligence technologies.

According to an embodiment of the present invention, a method of securely storing MCBFV in the right and left MCAs in data blocks so that it cannot be modified after storage comprises the steps of recording the data using an ultrasound device and at baseline and during performance of a standardized test for mental performance.

According to an embodiment of the present invention, a method of securely storing data in data blocks so that it cannot be modified after storage comprises the steps of building of the blockchain starting with the root (r) block encoding the laterality index (LI) calculated from both sides of the brain, and for each successive block in the blockchain.

According to an embodiment of the present invention, the MCBFV of the right and left MCAs are used as root or genesis block payload to be included as part of a root block; wherein a root block comprises the root block payload and a root header, computing a root data hash from at least part of the root block payload; creating the root header comprising at least the root data hash, a root timestamp, a root cryptographic nonce, a root proof standard, and a root data descriptor; computing a short hash from inputs of at least said root data hash, said root timestamp, said root proof standard, and said root data descriptor, but excluding said cryptographic nonce.

According to an embodiment of the present invention, a method and system to monitor mental performance using brain potentials during the tasks of mental performance to compute a root header hash from inputs of at least said root data hash, said root timestamp, said root proof standard, said root data descriptor, said root cryptographic nonce, and said fork header hash.

According to an embodiment of the present invention, a method and system to monitor mental performance using cerebral metabolic indices during the tasks of mental performance to compute a root header hash from inputs of at least said root data hash, said root timestamp, said root proof standard, said root data descriptor, said root cryptographic nonce, and said fork header hash.

According to an embodiment of the present invention, a method and system to monitor mental performance using cerebral blood flow velocity during odor processing to compute a root header hash from inputs of at least said root data hash, said root timestamp, said root proof standard, said root data descriptor, said root cryptographic nonce, and said fork header hash.

According to an embodiment of the present invention, a method and system to monitor mental performance using cerebral blood flow velocity during facial recognition tasks to compute a root header hash from inputs of at least said root data hash, said root timestamp, said root proof standard, said root data descriptor, said root cryptographic nonce, and said fork header hash.

According to an embodiment of the present invention, a method and system to monitor mental performance using cerebral blood flow velocity during the tasks of cognitive biometrics to compute a root header hash from inputs of at least said root data hash, said root timestamp, said root proof standard, said root data descriptor, said root cryptographic nonce, and said fork header hash.

According to an embodiment of the present invention, a method and system to monitor mental performance on a peer-to-peer distributed network of users working towards a solution to a given task, the LI of the mental-state-of being at the time of making the contribution is calculated in blocks and encrypted as harsh, and then added to the blockchain; after the harsh which is the cryptographic puzzle is solved by a computer in the network, it posts the solution to all other computers on the network, this is known as proof-of-work; once the proof of work is verified, the suggestion is accepted or otherwise rejected and the block LI is added to the consensus blockchain; the consensus blockchain comprises the LI data of mental-state-of-being that produced the valid path to the solution of the problem; the contribution of each person in the blockchain is attached to a smart contract, which is regarded as a secured stored procedure; its execution and codified effects like the transfer of intellectual property between parties are strictly enforced and cannot be manipulated, after a transaction with specified contract details is stored in the blockchain, and said transaction could be attached to a rewarding system including digital currency.

In one embodiment of the present invention, the data stored in blockchains include consensus blocks and the rejected blocks, are mined using standard methods of machine learning such as cluster analysis or clustering; in the exploratory mining, the blocks are used to form clusters, for example, consensus and rejected blocks, and subjected to statistical analysis.

In yet another embodiment, artificial neural networks (ANN) could be implemented in which the blockchains could form units or nodes called artificial neurons which model the aggregate effects of neurons in the brain of each person on the network; using the timestamps and other information in the block header the neurons could be ordered in a chronological and problem-phase sequence showing connectivity of one neuron to the other like synapses, that transmit a signal; the resulting structure has each neuron that receives a signal then processes it and can transmit the signal to other neurons connected to it; the ANN uses as the signal the LI at a connection which is a real number, and the output of each neuron is computed by some non-linear function of the sum of its inputs; these connections called edges with the neurons have weights that adjust as the learning proceeds; the weight increases or decreases the strength of the signals at each connection; using the data from the rejected blocks the neurons could have assigned thresholds such that a signal is sent only if the aggregate signal is within the limits of the set threshold; the neurons are functionally aggregated in different layers which perform different transformations on their inputs; the signal travels from the input layer traversing multiple layers to the output layer; the operator may implement supervised learning techniques to develop the initial learning function and learning algorithm (for example, support vector machines, linear regression, logistic regression, naïve Bayes, linear discriminant analysis, decision tree, k-nearest neighbor algorithm, neural networks multilayer perceptron, similarity learning etc.); the learning algorithm is ran on the collected training set, and cross-validation performed, to determine the accuracy of the learned function; the mental performance of the resulting function should be measured on a test separate from the training set.

The ANN structure is a complex graph of connected nodes as shown in FIG. 4. The internalization of environmental excitation in a node as well as inter-nodal neuro-signals transductions can be modeled by employing fuzzy functionality of the ANN could be illustrated by an example of the function of a computational model [Bagchi, 2015].

In one other embodiment of the present invention, a method and a system applicable in homeland security, for the training of immigration officers to recognize faces of dangerous terrorists entering through an airport; in the training sessions, the immigration officers are presented numerous faces of dangerous terrorists from an archive resident in the immigration server computer while monitoring the cerebral blood flow velocity in the brain arteries with U.S. Pat. No. 6,773,400 to Njemanze; a face that is recognized elicits a response LI that is different from a face unknown; using the present invention, the data of MCBFV is used to calculate the LI, which is stored in the blockchain; the consensus blockchain and rejected blocks are mined using ANN to determine positive matches and the information used to trigger computer-based facial recognition and other biometric data. Furthermore, data could be mined from a multi-dimensional blockchain, wherein, each network user or node could create a slidechain from which valid blocks could be added to the growth of the consensus blockchain. The ANN could mine data from all the blocks using customized protocol to differentiate valid from non-valid blocks. The U.S. Pat. No. 9,608,829 describes a method to create slidechain which allows for multiple valid branches or forks to propagate simultaneously with customized set of protocol rules embedded and applied to each fork chain that branches from another chain.

The foregoing summary of the present invention with the preferred embodiments should not be construed to limit the scope of the invention. It should be understood and obvious to one skilled in the art that the embodiments of the invention thus described may be further modified without departing from the spirit and scope of the invention.

One embodiment of the present invention would be illustrated using the cerebral blood flow velocity indexed by transcranial Doppler, however, anyone skilled in the art could program the calculations of these indices measured from brain electrical potentials, cerebral blood metabolism, cerebral blood flow or any other biophysiologic parameter indicative of mental performance, without departing from the spirit and scope of the present invention.

Figure 1:
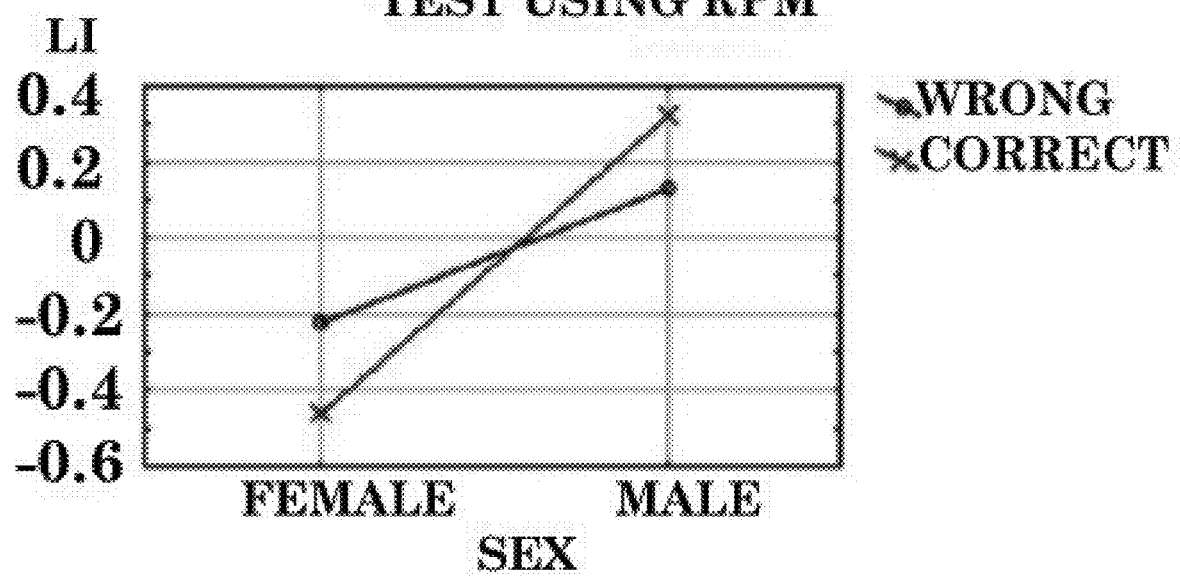
FIG. 1. Shows the changes with laterality index (LI) in female and male subjects in Wrong and Correct Responses during Raven's Progressive Matrices.

FIG. 1, shows the changes with laterality index (LI) in female and male subjects in Wrong and Correct Responses during Raven's Progressive Matrices. In males, Correct answers are associated with right lateralization, while Wrong answers are associated with tendency towards left lateralization. In females, on the other hand, Correct answers are associated with left lateralization, while Wrong answers are associated with tendency towards left lateralization.

Figure 2:
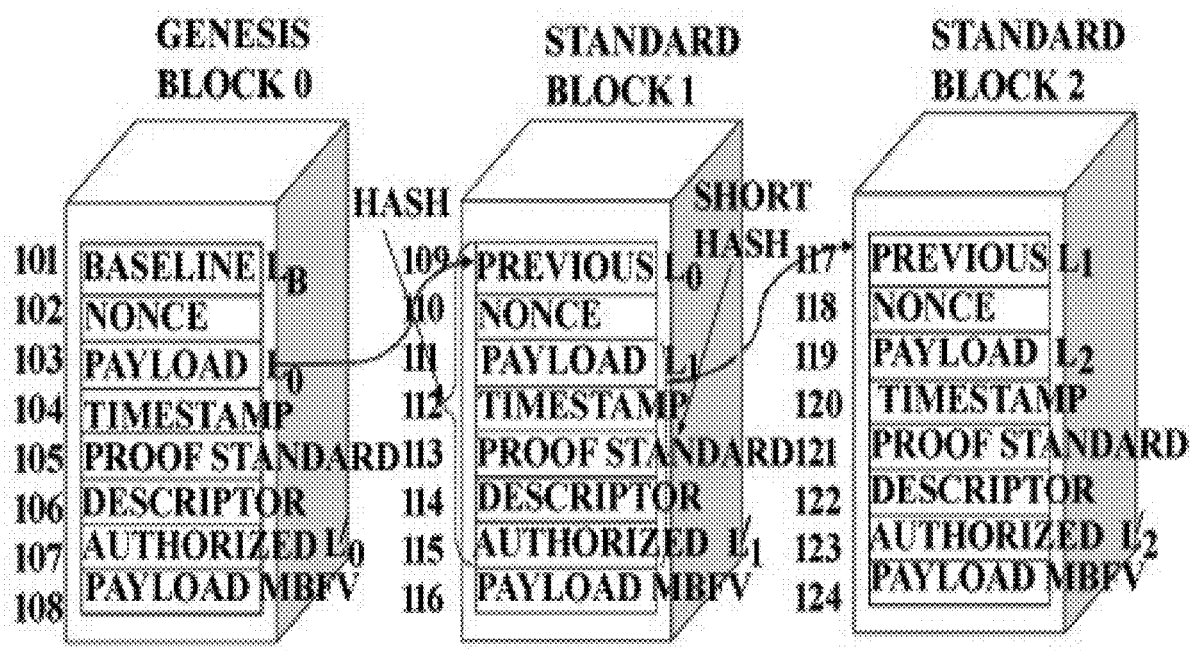
FIG. 2. Structure of the mental performance consensus blockchains formed. Each new block is added into the peer-to-peer network according to an embodiment of the present invention.

FIG. 2, shows the structure of the mental performance consensus blockchains formed. Each new block is added into the peer-to-peer network according to an embodiment of the present invention. The system records values of MCBFV at resting baseline and calculates the baseline laterality index ($LI_B$=Right $MCBFV_B$–Left $MCBFV_B$/Right $MCBFV_B$+Left $MCBFV_B$) as the root baseline hash 101. The root baseline hash is utilized to define the initial baseline mental state of being of the user prior to task. The payload hash 103 ($LI_0$=Right $MCBFV_0$–Left $MCBFV_0$/Right $MCBFV_0$+Left $MCBFV_0$) is calculated when the task administration commences. The nonce or 'number only used once' 102 is used to vary the data content of the genesis block 0, and the payload hash 103 is a simple hash ($LI_o$). The timestamp 104 marks the time of data recording that created the block within a certain range of error. The nonce 102 allows for a large number of different outputs to be produced by the hash function so that the hash will be less than the proof standard 105. The descriptor 106 describes the side label of recording. The authorized hash 107 is calculated as relative laterality index ($LI^t_0 = LI_0 - LI_B$), which indicates which blocks, identified by a hash, are allowed to chain off this block. The payload hash 103 is a simple hash ($LI_0$) calculated from the MCBFV data in the payload 108, and does not have to meet any proof standard. The laterality index calculation entails that, the payload hash ($LI_0$) is included as part of the input when the hash is calculated for the purpose of storing as the previous hash of the next block. According to one embodiment of the present invention, the distributed network of users checks the timestamp 104 on a standard time and relative to the time of the task posed and will reject any block that has possible errors in the timestamp 104. The descriptor 106 describes the side label of recording, the size and/or data structure of the payload 108. For example, the descriptor 106 could include label of the MCBFVs in the payload 103, showing side of the recording (RMCBFV and LMCBFV), in the right (RMCA) and left (LMCA) middle cerebral artery respectively, monitored at a depth (cm) of recording, and the task description and for what duration. The descriptor 106 may indicate the index of the first byte in the payload 108 and the size of the payload 108. The hash for the previous block 109 is calculated for $L_0$ in the standard block 1. The descriptor 106 may also store other information such as artifacts induced by excessive movements, which are relevant to the interpretation of the payload 108. The nonce 110 is used to vary the data of the standard block 1. In the standard block 1, the payload hash 111 is a simple hash ($LI_1$) is calculated from the payload of block 1, while the timestamp 112 marks the time the data was recorded. When calculating the hash 109 for the previous block, it must meet certain criteria defined by data stored as the proof standard 113, and the data labeled with the descriptor 114. The authorized hash 115 is calculated as relative laterality index ($LI^t_1 = LI_1 - LI_0$). The blocks relate to each other in a particular sequence. In the standard block, the previous hash 109 is the result of a non-reversible mathematical computation of the payload data 116 from the genesis block serving as the input. The hash function ($LI_1$) of the next standard block is derived in a similar manner. The design is such that any change to the data in the previous block results in an unpredictable change in the hash of that block. The previous hash 109 is what creates the link between blocks, chaining them together to form the blockchain. In one embodiment, the proof standard 113 could be set, so that the calculated hash must be less than 1, or at any other number selected by the protocol to forestall artifacts. The hashing function output is unpredictable, so it cannot be determined, before the hash is calculated, what input value will result in an output that is less than the proof standard 113. In the standard block 1, the payload hash 111 is a simple hash ($LI_1$) is calculated from the data in the payload 116, the timestamp 112 marks the time the data was recorded, and the descriptor 114 labels the data. The hash for the previous block 117 is calculated for $L_1$ in the standard block 2. The nonce 118 is used to vary the data of the standard block 2. Similarly, in the standard block 2, the payload hash 119 is calculated from the data in the payload 124, the timestamp 120 marks the time the data was recorded, as the proof standard 121 is set, so that the calculated hash must be less than 1, and the descriptor 122 labels the data. The authorized hash 123 is calculated as relative laterality index ($LI^t_2 = LI_2 - LI_1$). Anyone of ordinary skill in the art would recognize there are a variety of different proof standards that could be used. The proof standard could be based on proof of work, such as hash value requirements or any other kind or proof of consensus. The proof standard may be applied as a rule that requires a hash value to be less than the proof standard, more than the proof standard, or have a required bit sequence or a required number of leading or trailing zeroes. Any proof standard may be used without departing from the spirit and scope of the present invention.

Figure 3:
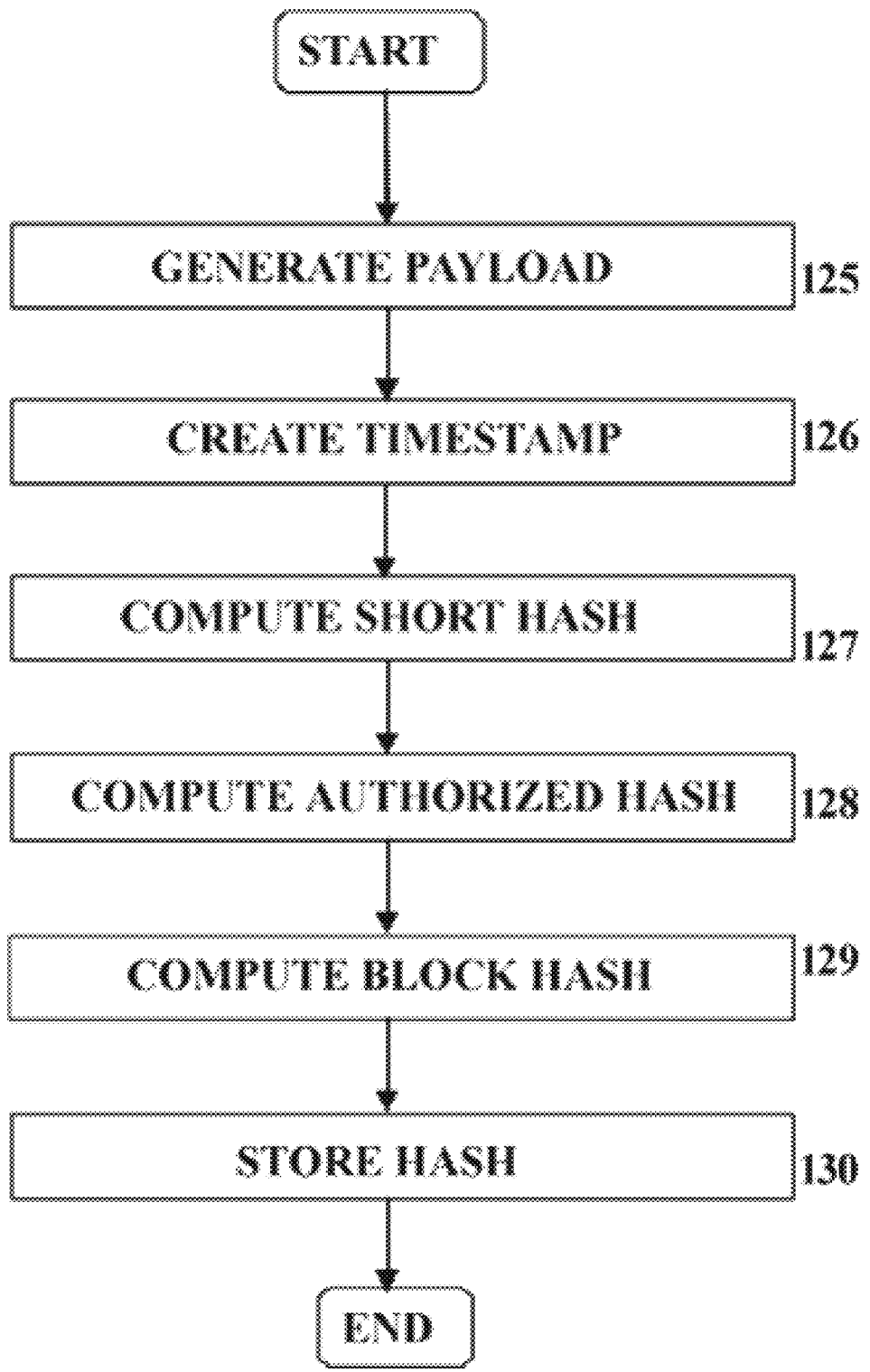
FIG. 3. Flowchart for the process of creating a valid blockchain according to an embodiment of the present invention.

According to an embodiment of the present invention, FIG. 3 shows a flowchart for the process of creating a valid blockchain. At step 125, the system computes the payload from MBFV recording. The payload hash is a mathematical computation of LI from the payload data and does have to meet the criteria of proof standard. At step 126 the system gets a timestamp. The peer-to-peer network follows protocol rules for accepting new blocks that require the timestamp to be within a certain range. A timestamp that appears invalid or faked will result in rejection of the block by the distributed network. At step 127, the short hash for the block is computed. The short hash for the block uses at least the payload hash and timestamp as inputs, and may include other parts of the block as well. At step 128, the authorized hash in the block is computed. At step 129, the block hash for the block is computed. The block hash must meet the proof standard stored. This is accomplished by repeatedly adjusting the nonce until a hash is found that meets the proof standard. At step 130, the block hash from the block is stored, to be used as the previous hash in the next block, and then the program ends. The successive blocks have similar steps.

Figure 4:
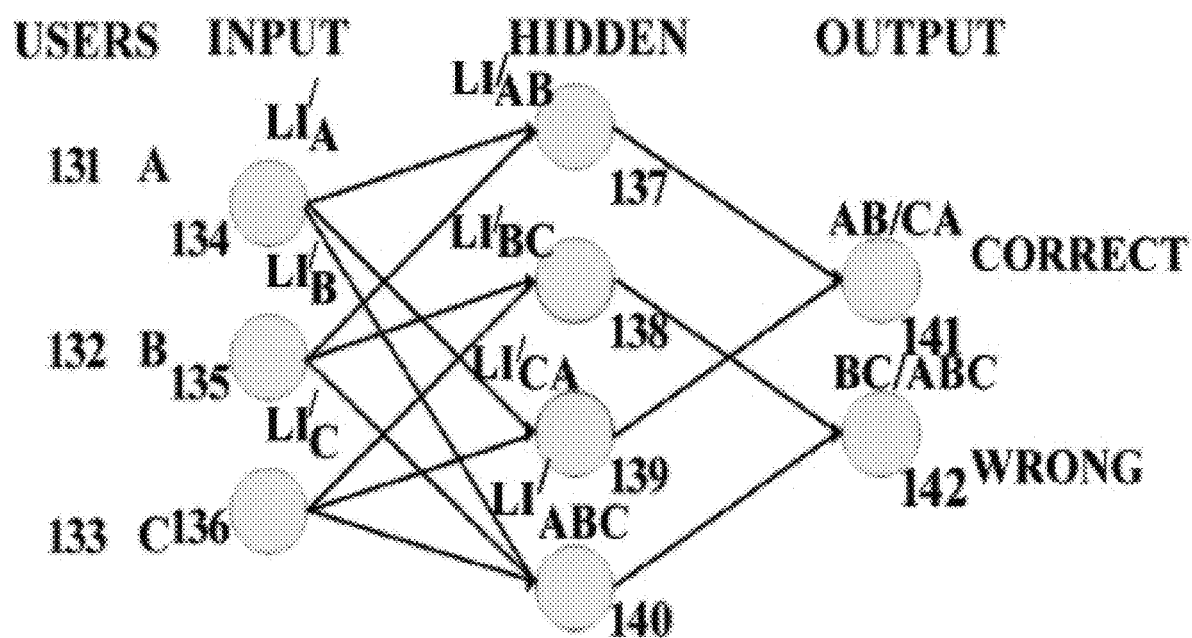
FIG. 4. Structure of the artificial neuronal network topology of a peer-to-pear network according to an embodiment of the present invention.

FIG. 4, shows the structure of the artificial neuronal network topology of a peer-to-peer network according to an embodiment of the present invention. According to an embodiment of the present invention, FIG. 4, shows the artificial neural network (ANN) of the feedforward topology representing three peer-to-peer network user A 131, user B 132, and C 133, from which the mental performance indices $LI^I_a$ 134, $LI^I_b$ 135, and $LI^I_c$ 136, were mined during the initiation of problem solving as the input neurons in the brain. These nodes could interact with each other during the problem-solving in a combinatorial manner to yield a new level of hidden neurons or nodes $LI^I_{ab}$ 137, $LI^I_{bc}$ 138, $LI^I_{ca}$ 139, $LI^I_{abc}$ 140, which then produces an output of Correct 141, or Wrong 142, at each node value or activation. Each link is associated with weight. If the distributed network generates the correct response there is no need to adjust the weight. Conversely, when the output is wrong then the ANN learns to adjust the weights. In the case of human deficiency in the task, the human-robotic interface would detect the node at which the deficiency occurred and provides the needed information and to fill-in for the deficiency. The human-machine or human-robotic interface performs the task after machine learning to adjust the weights. The ANN learning could occur by supervised learning, unsupervised learning, and reinforcement learning. Other methods of machine learning include, back propagation algorithm, Bayesian networks that use probabilistic dependencies, and other methods of machine learning.

Figure 5:
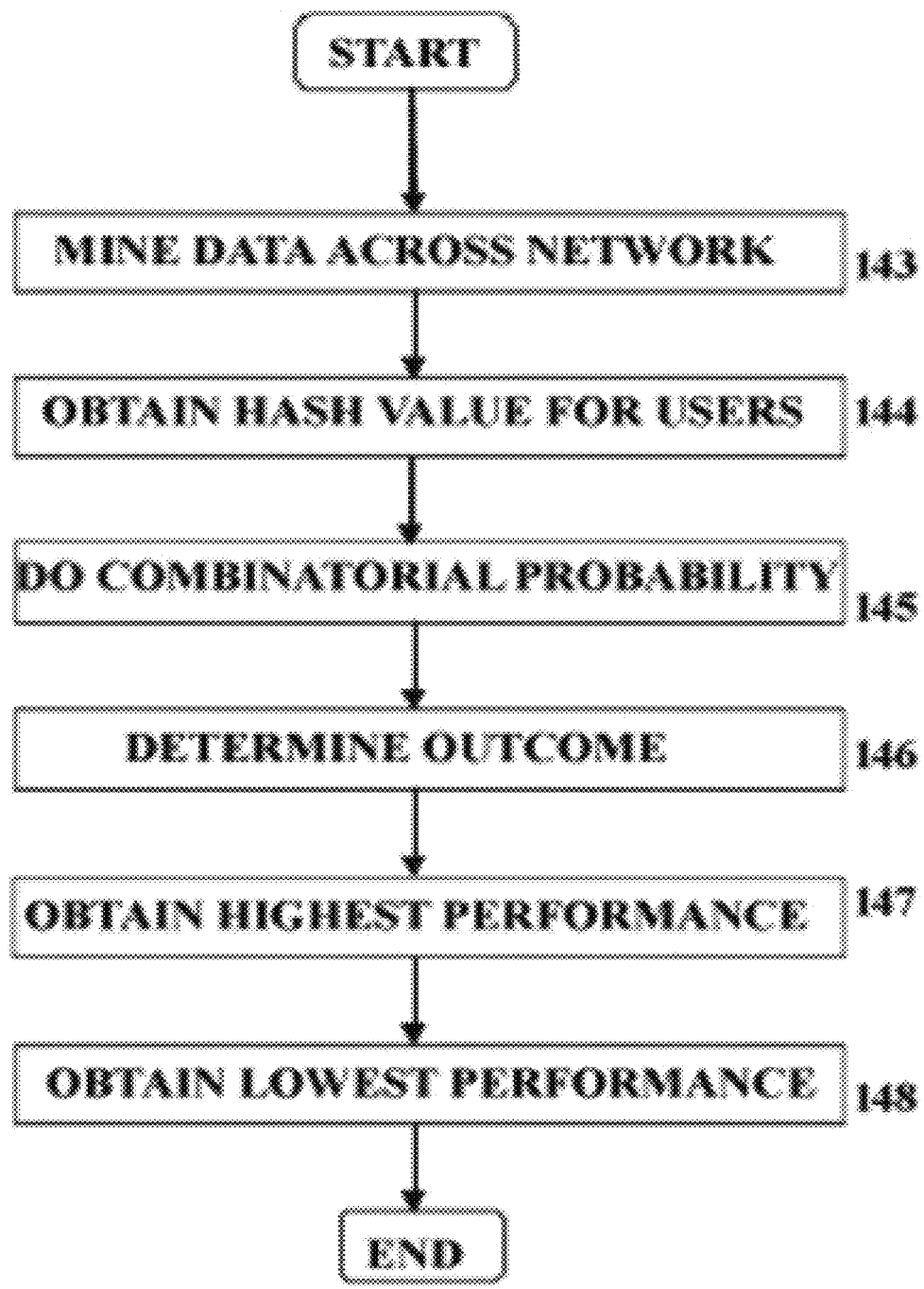
FIG. 5. Shows a flowchart for mining data in a valid blockchain with artificial neural network, which creates combinatorial probability from input nodes to performance outcomes.

FIG. 5, shows a flowchart for mining data in a valid blockchain with artificial neural network, which creates combinatorial probability from input nodes to performance outcomes. According to an embodiment of the present invention, FIG. 5 shows a flowchart for mining data in a valid blockchain with artificial neural network which creates combinatorial probability from input nodes to performance outcomes. At step 143, the system mines the data from blocks across the network. The data obtained comprises the computed hashes 144, from across the network. At step 145 the system obtains the interactive combinations of the various nodes, and proceeds to obtain the combinatorial probability towards positive and negative outcomes 146. The system determines the viable combinations that led to highest performance 147, and those that led to lowest performance 148.

Figure 6:
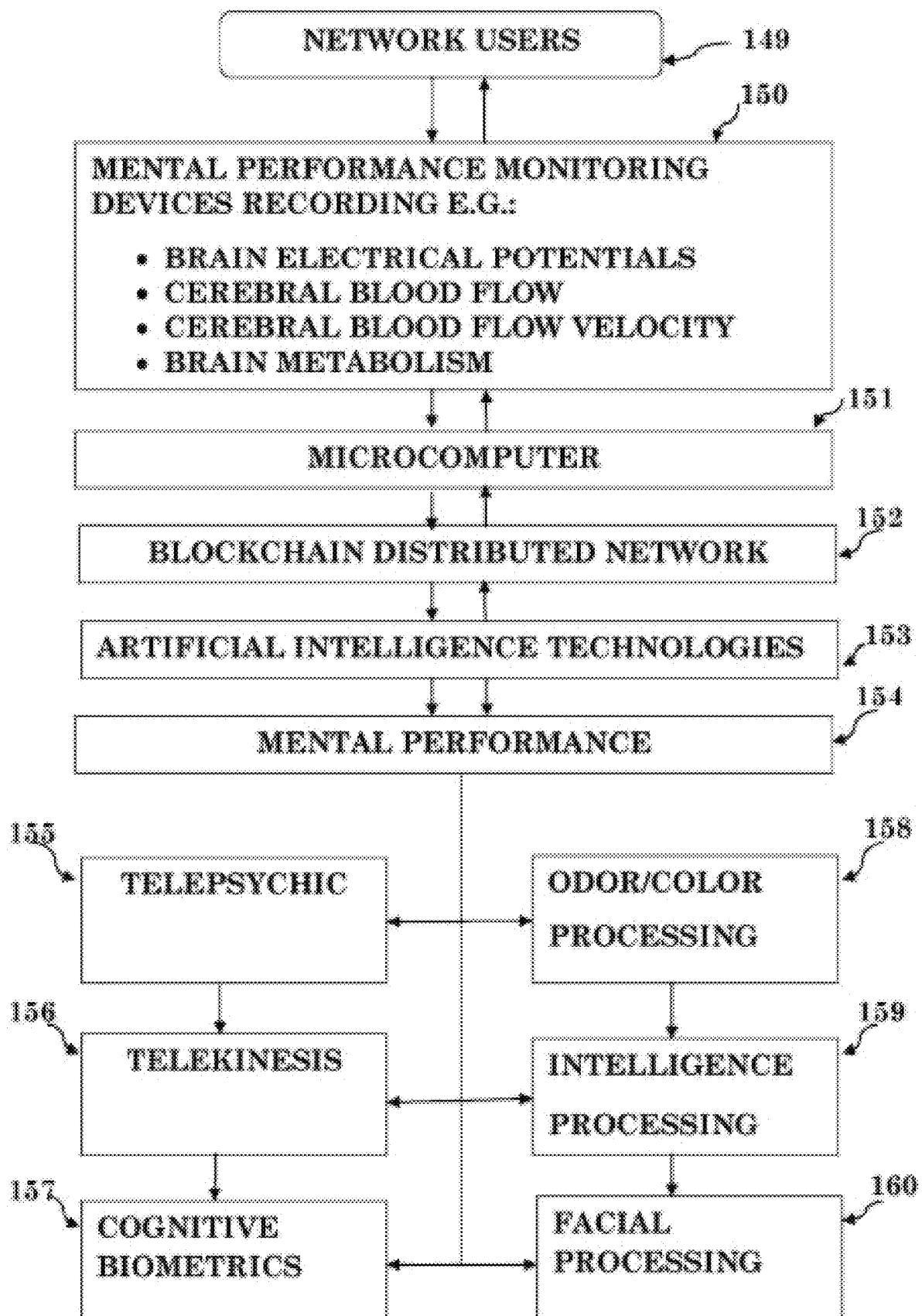
FIG. 6. Shows an embodiment of the equipments of the present invention, assembled to include means of recording the mental state-of-being of network user or users.

FIG. 6, shows an embodiment of the equipments of the present invention, assembled to include means of recording the mental state-of-being of network user or users. According to the afore mentioned descriptions, in summary, an embodiment of the equipments of the present invention, FIG. 6 could be assembled to include means of recording the mental state-of-being of network user or users 149 by applying but not limited to means of recording 150 of brain electrical potentials, cerebral blood flow, cerebral blood flow velocity, brain metabolism or similar indices of brain activity. The data is recorded on a microcomputer 151 which could include an optical computer, quantum computer, analog computer or others that perform similar functions. The data is shared across a secure blockchain distributed network 152, from which data could be mined using AI technologies 153. The data could be used for mental performance monitoring 154, that could include but not limited to telepsychic control 155, telekinesis for telerobotic control 156, cognitive biometrics 157, odor and color processing 158, intelligence processing 159, and facial processing 160, that could used to validate identity in highly secured networks including those used by the military or for financial transactions with digital currency on blockchain, and could further include language, visual, smell, pain, touch, and proprioception areas of the brain.

Figure 7:
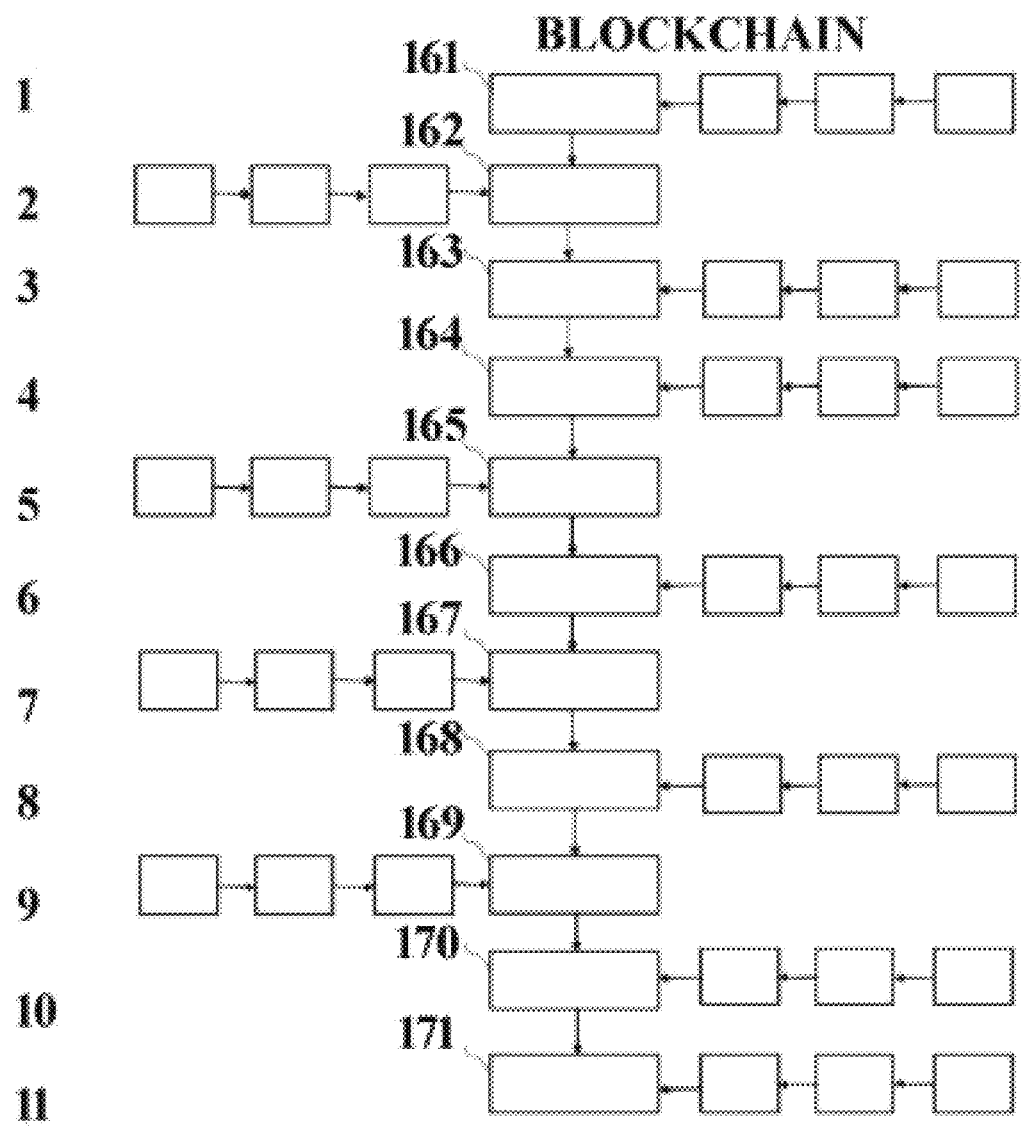
FIG. 7. Shows each node (1-11) mined from the slide-chains and consensus blockchain.

FIG. 7, shows each node (1-11) mined from the slidechains and consensus blockchain. In FIG. 7 of the illustration, each node (1-11) is mined from the slidechains and consensus blockchain from node 1, 161, node 2, 162, node 3, 163, node 4, 164, node 5, 165, node 6, 166, node 7, 167, node 8, 168, node 9, 169, node 10, 170, and node 11, 171. The system implements computer hardware and software which may include computer executable code in a variety of languages including without limitation C, C++, Java, JavaScript, Python, Prolog, assembly language, Lisp, HTML, Perl, etc.

Figure 8:
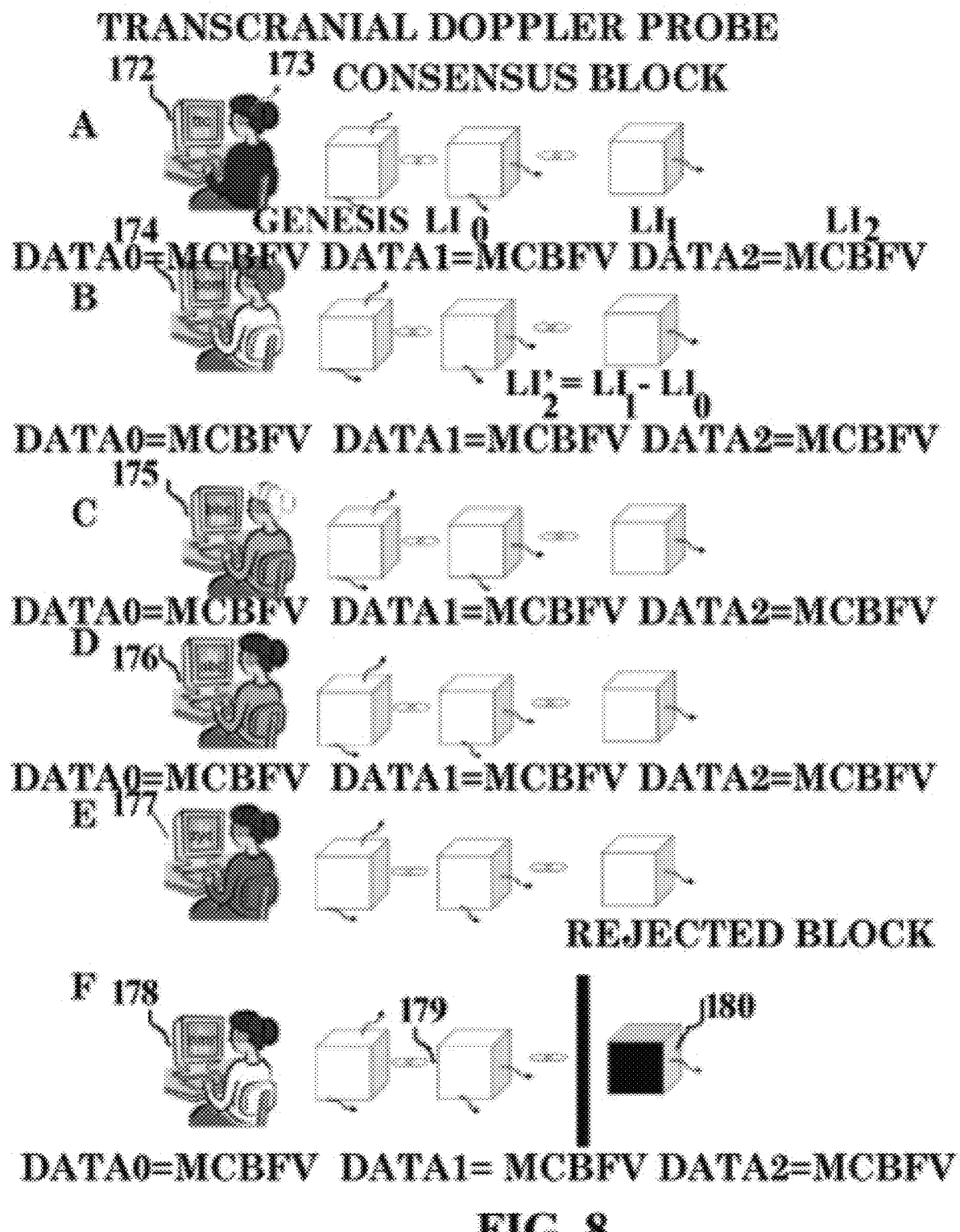
FIG. 8. Shows the schematic diagram of persons working as nodes on the distributed network shown in FIG. 7.

FIG. 8, shows the schematic diagram of persons working as nodes on the distributed network shown in FIG. 7. Each person A, working on a computer node 172, is affixed to a head-gear with a transcranial Doppler ultrasound probe 173 for monitoring MCBFV, the said positions of the arteries monitored are stored on a slidechain, and contributes blocks comprising data hash calculated from the payload MCBFV at timestamp $t_{0, 1, 2 \ldots}$, that are accepted into the consensus blockchain; person B, working on a computer node 174, contributes another set of blocks comprising data hash derived from payload MCBFV at timestamp $t_{0, 1, 2 \ldots}$, to the consensus blockchain; person C, working on a computer node 175, contributes a set of valid blocks comprising data hash derived from payload MCBFV at timestamp $t_{0, 1, 2 \ldots}$, to the consensus blockchain; person D, working on computer node 176, contributes another set of accepted blocks comprising data hash derived from payload MCBFV at timestamp $t_{0, 1, 2 \ldots}$, to the consensus blockchain; person E, on the computer node 177, contributes yet another set of valid blocks comprising data hash derived from payload MCBFV at timestamp $t_{0, 1, 2 \ldots}$, to the consensus blockchain; however, the person F, at computer node 178, contributed invalid blocks 179, which are rejected 180.

Figure 9:
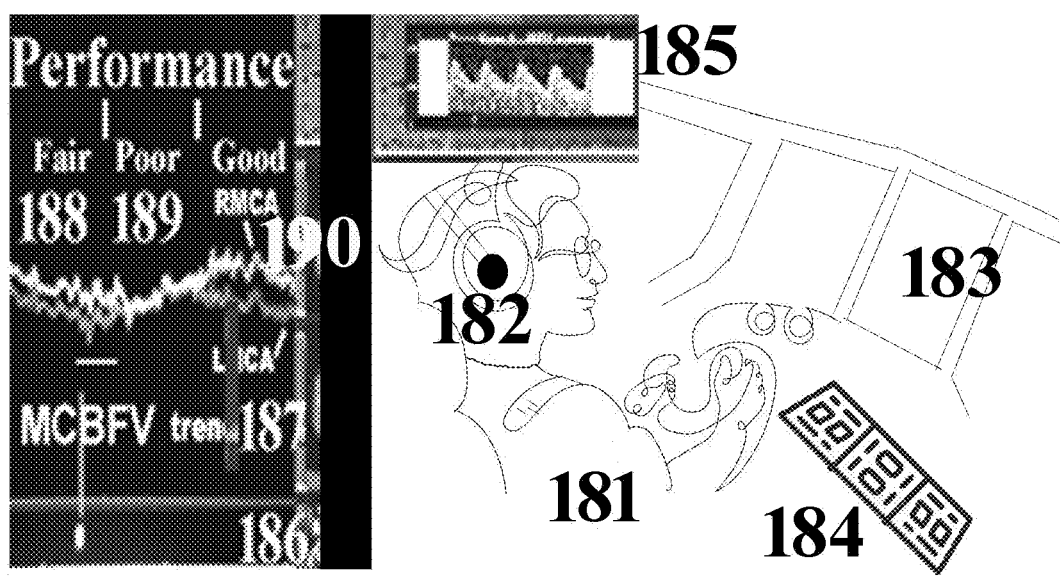
FIG. 9. Shows the picture of a pilot with head-gear integrated with MCBFV monitoring device as a node of a human-high performance avionic interface.

FIG. 9, shows the picture of a pilot with head-gear integrated with MCBFV monitoring device as a node of a human-high performance avionic interface. The pilot 181, wearing a head-gear integrated with a transcranial Doppler ultrasound probe (MCBFV) or optical laser Doppler probe or any other means to monitor brain blood flow 182, pre-flight, in-flight and post-flight. The MCBFV is monitored as the pilot engages with flight tasks. Simultaneously, as the pilot makes visual contacts with targets 183 and observes aircraft dashboard displays 184, the MCBFV 185 is monitored, on the same timeline 186, while tracing the trend of MCBFV 187 in the right (RMCA) and left (LMCA) middle cerebral arteries during different levels of performance ratings as it varies from 'Fair' 188, to 'Poor' 189 to 'Good' 190. The payload MCBFV is used to calculate the data hash for the blocks formed for different performance ratings. The data is mined with AI techniques to determine patterns associated with different levels of mental performance. The system uses the changes in cerebral blood flow velocity to regulate the autonomy-decision-making level between the pilot and autopilot. The AI technology uses the data calculated from the MCBFV to determine if the performance is 'Good', then the pilot has full autonomy for decision-making, as the performance becomes 'Fair', there is a shared pilot-autopilot decision-making, but when the pilot performance falls to 'Poor', then the autopilot system takes full control of decision-making and relating to ground-control center.

Figure 10:
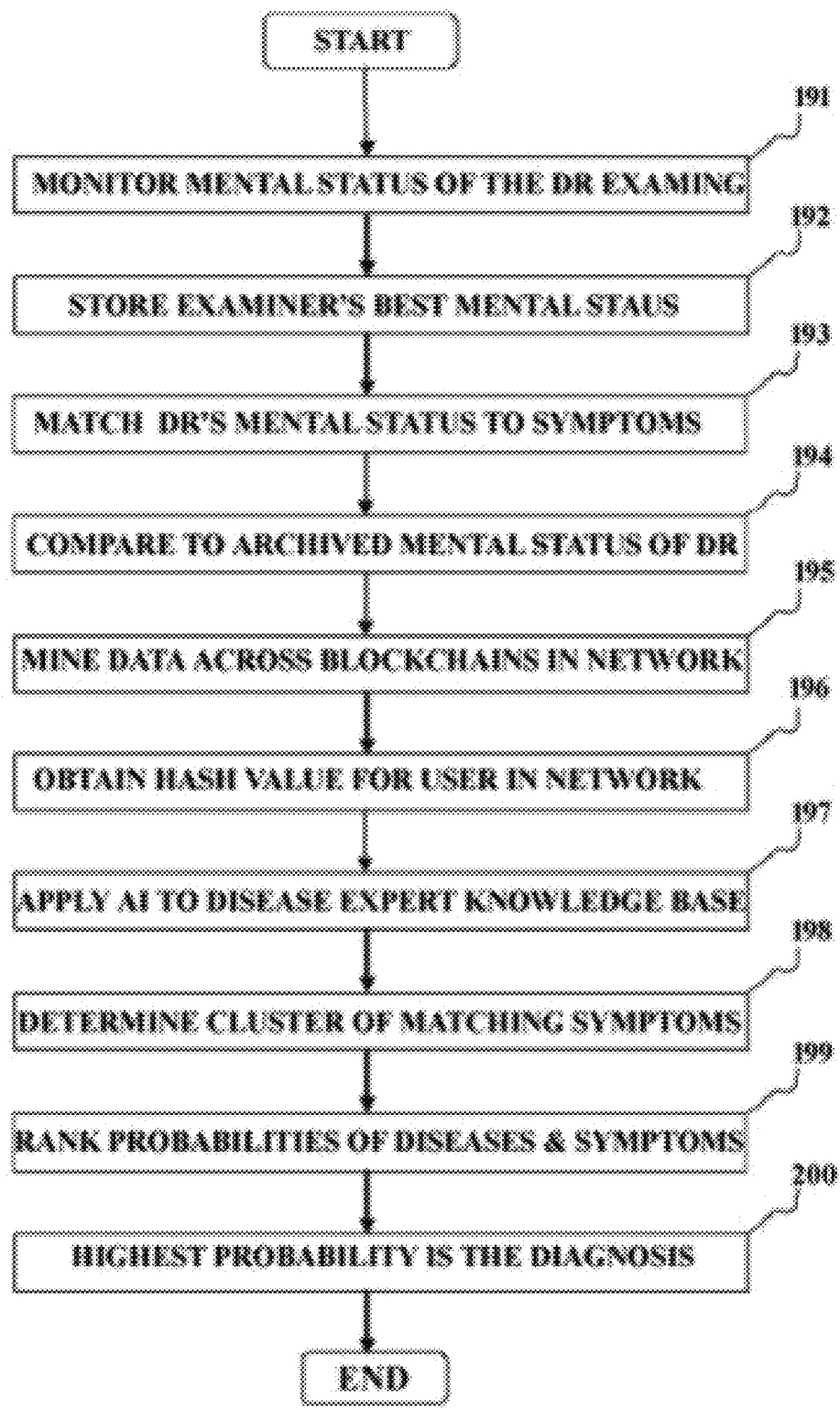
FIG. 10. Shows an example of the flowchart of use of the present invention for medical expert knowledge system.

FIG. 10, shows an example of the flowchart of use of the present invention for medical expert knowledge system. The system starts to consider if the medical examiner is in the 'best' mental state-of-being to make a good evaluation of the patient's symptoms and compares the decision-made to archival data of the medical expert knowledge base. The mental status of the medical examiner is monitored during evaluation 191, and data stored in the blockchain, noting if the mental state-of-being for best performance 192 was attained, during assessment of patient's symptoms 193, which is then compared to archived data of mental status of past decision-making by the examiner and also compared to that of other medical experts during similar evaluations 194. The AI system proceeds to mine all the data stored in the blockchain 195, by obtaining the hash value for each user in the network 196, and applying AI technologies to the disease expert knowledge base to associate symptoms and signs to disease 197, in order to determine a select cluster of matches of symptoms to disease 198. The matches of symptoms to disease are then ranked by probabilistic analysis 199, to determine the highest probability as the most likely diagnosis 200, at the end.

The steps illustrated in the flowcharts need not be executed in the order described. Anyone of ordinary skill in the art would recognize that the order of certain steps can be rearranged without departing from the spirit and scope of the present invention. A variety of embodiments are disclosed, still other embodiments of the present invention will become apparent to those skilled in the art from this detailed description. The present invention could be modified in various obvious aspects, all without departing from the spirit and scope of the present invention. Accordingly, the drawings and descriptions are only illustrative in nature and not restricted to the examples given.

Practical Applications of Mental Performance Determination Using Blockchain and Artificial Intelligence Technologies.

One application is to make use of the information to upgrade or downgrade the autonomy-decision making level of each node and determine options of combinations with highest efficiency. The system could determine the options in a local area network (LAN) of one of just a few users, a wide area network (WAN) of many users or from thousands of users on the Internet. The programmer could make use of the information in many ways as desirable including but not limited to changing autonomy-decision making levels between user/operating system, self-driving car/designated driver, human/robotic systems, human/machine interface, pilot/autopilot, gamer/game control, peer-to-peer on a distributed network, cognitive biometrics, air traffic controller/central computer etc.

The present invention could be applied to create intelligent operation systems (OS) and software on personal computers that detects the mental state-of-being of a user, and when compromised the OS or software activates library sources on the system or through the internet to assist the user. This would improve the quality of word processors, mathematical programs and other types of programs applicable in many fields. For example, if a lawyer is preparing a case brief, the AI word processor of the present invention detects compromise in performance, the system could from the aforementioned citations, provide hyperlinks to similar citations on the internet. Similarly, application could be used by a scientist working on a scientific paper. The AI word processor could do this by intentionally prompting by the user for assistance on detection of mental performance compromise.

The present invention could be used to predict high probability of success in a given task by many users. The combinatorial probability determination provides an enhanced peer-to-peer collaborative work. The mental state-of-being of one user may enhance that of the other user in a productive way. Such mutual enhancement is needed in a network of users with different capabilities. Some users like immigration officers at the airport might have a high ability to recognize faces, others have a very good sense of smell and yet others a very good memory of events. The present invention could be applied to test the mental performance in the different domains to constitute the teams in a more productive manner.

The present invention could be applied to improve security and prevent terrorism. For example, a military pilot with certification to fly a military plane who became radicalized by fundamentalists has conventionally valid biometrics of fingerprint and facial recognition. The present invention could be applied to obtain cognitive biometrics which monitors the mental state-of-being during normal uneventful flight operations of the pilot. The concept of cognitive biometrics assesses mental fitness of the person to perform a given task in real-time, rather than just the biometric parameters of facial recognition, finger print, voice recognition and others. The said person must be certified in 'good mental state-of-being' for the task. Such that, if the intention is to cause harm like delivering a bomb to the 'Pentagon' building, the motive would elicit a change in mental state-of-being long before the actual time of the terrorist activity. While normal biometrics would certify the pilot as fit-to-fly, the cognitive biometrics would detect significant changes in mental state-of-being, with high probability of negative outcome. The autopilot within the aircraft would downgrade the autonomy decision-making level of the pilot, and could declare the pilot unfit to fly even before flight or even when in-flight reject commands to deliver the bomb payload.

The present invention would significantly improve the security of use of the blockchain technology for financial transactions. The state of the art is based on trust that the peer-to-peer network are between two parties acting on free will to make a legal transaction. While the blockchain provides the ease of transaction, the cyberterrorist could use the system for extortion. A person could be kidnapped and forced to make a financial transaction to another person without alerting the authorities across borders. However, the present invention when implemented would determine the mental state-of-being of the both parties and permits transaction when both parties are certified to be in a good mental state-of-being in real-time monitoring.

The present invention could be implemented with self-driving car technology to significantly reduce road traffic accidents. The unpredictable accidents that could arise on the highway and natural disasters would create a situation whereby, for self-driving car technologies to be implemented, there must be a designated human alternative driver. In such a situation the present invention is used to monitor the mental state-of-being of the driver and when compromised the self-driving car takes over control to assure safety. For example, a human driver may sleep off during a long trip and the mental state-of-being could detect the sleep pattern and the self-driving car can take over until full wakefulness is assured. Similarly, a drunk driver could be detected from mental state-of-being and smell of ethanol from sensors in the self-driving car, the auto-driver would take over control of the car until the passengers are brought to safety.

The present invention could be implemented in a factory where humans and robots work together as a team. Humans could get tired and lose concentration at work which could be detected as changes in mental state-of-being. The state of the art has no means of relating the robotic systems to the humans at the same workplace, hence, there is no effective human-robotic interface as regards mental performance of the human. The present invention remedies this human-robotic disconnect by allowing detection of the mental state-of-being of the human and communicates same to the robotic system. The robotic system takes over control at these critical times of low human performance to ensure efficiency at the workplace.

The present invention could be utilized to compute the differences between over one trillion odors that the human nose can differentiate. The state of the art such as the U.S. Pat. No. 6,663,571 to Njemanze describes an apparatus that uses transcranial Doppler to differentiate mental processing of odors. However, the '571' patent does not show how the several millions of possible options could be computed. The present invention using machine learning could differentiate multiple responses of the human brain to different odors and recognition of a target odor. The same technology could be implemented at seaports, where trained dogs are released to perceive odors in containers with the target odor such as contents with TNT explosives. The port inspectors could implement the present invention to see when the target odor pattern is detected in the brain of the canine. For example, a dog wearing the device described in the '571' patent attached to a GPS could have the recordings of MCBFV taken at the point of detection of the odor, and the data processed using the present invention with AI to recognize the pattern associated with the odor of TNT. The security agents could now use the GPS coordinates to locate the container with TNT explosives hidden at the seaport.

The present invention could be utilized by designers to assess the reaction to their latest designs and the color effects. The U.S. Pat. No. 8,152,727 to Njemanze describes a method for assessment of color processing mechanism in the human brain for diagnosis and treatment. The device of the '727' patent could be used to acquire mental performance data in response to the different designs, and link it to 'likes' and 'dislikes.' However, the state of the art does not describe any practical ways to process the data acquired for practical implementation. The present invention could be used to train the AI using big databases from different people of different cultures and traditions; a consistent mental performance pattern could be established. Subsequently, using the present invention, just a few target groups could be used to assess the effectiveness of cloth designs, creative artistic paintings, adverts, concerts, color books, music, drama, political presentations, TV programs, etc.

The present invention could be utilized by security agents to assess and detect the faces of dangerous criminals at a port of entry; for example, measurements of MCBFV data during facial processing in the security agent could be performed with the U.S. Pat. No. 6,773,400. The transcranial ultrasound probe is within a head-gear controlled by artificial intelligence placed on the temporal bones of the agent as described in U.S. Pat. No. 6,547,737. The optimal angles of insonation of the arteries obtained with the device of the '737' patent could be stored in blocks of the slidechain. The data is mined with the AI techniques of the present invention to determine the optimal angles of insonation of the arteries of the brain, and ultimately to determine the matching responses during facial recognition, in order to trigger confirmation using computer-aided facial recognition software of a cognitive biometric system.

Several degenerative diseases and depression cause measurable changes in cerebral blood flow. The U.S. Pat. No. 7,942,820 to Njemanze P. C. describes a method and system for evaluation and treatment of depression. However, the '820' does not show how to compute the data to determine patterns of variations associated with the different types of depression and degenerative diseases. The present invention implements blockchain and AI technologies to determine patterns of mental performance including in patients with depression and degenerative diseases for early diagnosis and to monitor effectiveness of treatment regimen.

The present state-of-the art uses empirical psychological tests to evaluate mental performance of subjects. It is usual to test general intelligence using Raven Progressive Matrices (RPM). Njemanze (2005) has demonstrated that it is accompanied by specific changes in cerebral blood flow velocity. The U.S. Pat. No. 6,390,979 demonstrated the use of MCBFV to determine changes during mental performance. The present invention could be used to track subtle changes associated with mental performance using MCBFV or other parametric measures such as brain electrical potential, cerebral blood flow and metabolism. The present invention records and securely stores the mental performance of different states in the blockchain, from optimal performance to that under different stressful conditions associated with compromised mental performance, and then utilizes AI technologies to recognize each state for appropriate categorization including under real-time conditions.

The present invention could be used to integrate human-robotic interface to train intelligent robotic dexterity or use of robotic arms. In the case of occurrence of a nuclear accident and humans cannot work directly in the environment, there would be need to deploy robots. For example, the mental performance changes that occur during brain-eye-hand coordination movements by a skilled person operating the gears of a complex machinery such as earth moving equipment is recorded by a device such as that described in U.S. Pat. No. 6,390,979, or brain electrical potentials or brain metabolism. The present invention processes the data using blockchain and AI technologies to detect patterns of changes associated with each movement. Each brain-eye-hand coordination movement of a gear is translated into a set of commands to operate the robot. This could be translated into visual-eye-hand coordination feed-forward and feed-back commands to control the robot. In some cases, the skilled operator could guide the robot by performing the task at a remote place on virtual reality, while the robot at the site telemetrically obtains the changes in the mental performance of the skilled operator, which it translates into robotic dexterity commands to move the gears of the earth moving equipment at the radiation site. This could be described as robotic telekinesis.

The present invention processes mental performance contribution to problem solving, which could constitute materials used for transfer of intellectual property between parties in a codified manner that could be strictly enforced after a transaction with specific contract details stored on the blockchain attached to a smart contract. The securely stored mental performance activity in the blockchain is subject to the contract of intellectual property exchanges. The said intellectual exchanges could be attached to a reward system including use of digital currency. It solves the problem of theft of intellectual property on the internet across borders, although new legal instruments such as internet international copyright laws and patents would have to be specifically developed to enable enforcement.

The present invention could be applied to prevent stroke and heart attacks in patients by detecting microembolic signals using implantable transcranial Doppler ultrasound as described in the U.S. Pat. No. 6,468,219. The present invention securely stored the cerebral blood flow velocity signals in the blockchain and applies pattern recognition using AI technologies to detect the microembolic signals and automatically triggering the implanted pump to inject anti-coagulant into the patient, saving valuable time for prevention of strokes and heart hearts. The '219' patent required cross-checking the patterns with the doctor by telemetric transfer, however, this prolongs the time from detection of the embolus to treatment. The present patent, securely stores the cerebral blood flow velocity waveforms using blockchain technology as the payload data acquired in real-time, and the data hash mined using AI technologies for pattern recognition of the signals associated with microembolic detection. Such use of AI for emboli detection and lysis could be described as artificial intelligence embolysis (AI Embolysis).

The present invention could be used to track mental performance in physically and mentally challenged persons even in those who are blind, unable to speak or write. The progress in mental performance of the physically and mentally challenged children in school could be a major challenge and tracking progress with new teaching aids is still empirically assessed. The present invention could be used to track improvements in mental performance in the physically and mentally challenged and assessment of teaching techniques done in real-time. The responses to increasing levels of task complexity could be the criteria for assessment of effectiveness of training procedures.

Similarly, persons in vegetative state, at different levels of consciousness and sleep could be assessed even when they are incapacitated and unable to communicate using the present invention. The security of the blockchain and the data mining with AI technologies have added advantages to exclude any possible manipulations. Transcranial Doppler monitoring could be used to record cerebral blood flow velocity in patient in vegetative state and the present invention applied to process the data. The sensory responses to faces, color, odor, mental tasks, and sleep patterns provide criteria for assessment of the different spheres of mental state-of-being. It is hoped that, the findings using the present invention would be crucial to the medical decision that the patient is completely 'brain dead' or not, and staging of progress. The security of the data storage using blockchain and the pattern recognition of the changing mental states using AI technologies, makes the present invention indispensable as a future means of characterizing vegetative states using data from cerebral blood flow, cerebral blood flow velocity, brain metabolism or brain electrical potentials.

The invention claimed is:

1. A method of securely storing parametric measures of mental performance data across a network in a multi-dimensional distributed database, said method comprising the steps of generating a blockchain comprising linked data blocks, said blockchain being configured to determine the mental state-of-being of the network user which constitutes a node at the time of making valid or invalid contributions, and propagated to add to the consensus blockchain, wherein said growth occurs by adding new data blocks awarded to the consensus blockchain each time a participating node in the network makes an accepted mental performance contribution which propagates a block with corresponding block hash, said block comprising a specified set of protocols that determines the procedure for block data calculation, storage, interpretation, validity of consensus blockchain, sets criteria for generating a new block and its relationship with the previous block, wherein the blockchains form units or nodes called artificial neurons which model the aggregate effects of neurons in the brain of each person on the network creating artificial neural network.

2. The method of claim 1 further comprising the steps of: creating the artificial neural network that uses as the signal the data hash at a connection, and the output of each neuron is computed by some non-linear function of the sum of its inputs; these connections called edges with the neurons have weights that adjust as the learning proceeds; the weight increases or decreases the strength of the signals at each connection.

3. The method of claim 1 further comprising the steps of: using the data hash from the blocks as the neurons with assigned thresholds such that a signal is sent only if the aggregate signal is within the limits of the set threshold; the neurons are functionally aggregated in different layers which perform different transformations on their inputs; the signal travels from the input layer traversing multiple layers to the output layer; the operator may implement supervised learning techniques to develop the initial learning function and learning algorithm such as support vector machines, linear regression, logistic regression, naïve Bayes, linear discriminant analysis, decision tree, k-nearest neighbor algorithm, neural networks multilayer perceptron, similarity learning and others; the learning algorithm is ran on the collected training set, and cross-validation performed, to determine the accuracy of the learned function.

4. The method of claim 1 further comprising the steps of:
Creating blockchain and slidechain rule sets for obtaining data hash for mental performance using payload data from measures of brain electrical potentials.

5. The method of claim 1 further comprising the steps of: creating blockchain or slidechain rule sets for obtaining data hash for mental performance using payload data from measures of cerebral blood flow.

6. The method of claim 1 further comprising the steps of: creating blockchain and slidechain rule sets for obtaining data hash for mental performance using payload data from cerebral blood flow velocity measurements.

7. The method of claim 1 further comprising the steps of: creating blockchain and slidechain rule sets for obtaining data hash for mental performance using payload data from measures of brain metabolism.

8. A system for securely recording and storing mental performance data across a network in a multi-dimensional distributed database, said system comprising:
microprocessor;
a non-volatile computer memory storing computer readable instructions configured to:
generate a blockchain comprising linked data blocks, said blockchain being configured to determine the mental state-of-being of the network user which constitutes a node at the time of making valid contributions, and propagated to add to the consensus blockchain, wherein said growth occurs by adding new data blocks awarded each time a participating node in the network makes an accepted mental performance contribution which propagates a block with corresponding block hash, said block comprising a specified set of protocols that determines the procedure for block data calculation, storage, interpretation, validity of consensus blockchain, sets criteria for generating a new block and its relationship with the previous block, said blockchain could be configured to propagate for each node, branches of the slidechain, wherein a copy of said slidechain is distributed to every node in the network, and said one or more new blocks are propagated when a node in the network provides a valid mental performance contribution to the solution of the problem along with proof of work for the valid contribution, and a rewarding system for the valid contributions, wherein data stored in a block cannot be modified without invalidating all subsequent blocks.

9. The system of claim 8 wherein said computer readable instructions are further configured to:
create the artificial intelligence computational model of the mental performance, said mental performance could be used to regulate autonomy-decision-making levels in human-computer interface such as in self-driving cars, auto-pilot, human-robotic systems, cognitive biometrics for purposes of identification, cybersecurity, prediction of future actions, optimization of work efficiency.

10. The system of claim 8 wherein said computer readable instructions are further configured to create the artificial intelligence computer model of mental state-of-being through combinatorial probabilistic analysis of the nodes, that could be clustered to provide solution to a given problem, associated with a rewarding system for a valid contribution.

11. The system of claim 8 wherein said computer readable instructions are further configured to: create the artificial intelligence computer model of the mental state-of-being during odor, object form and color processing.

12. The system of claim 8 wherein said computer readable instructions are further configured to:
create the artificial intelligence computer model of the mental state-of-being during performance of a face detection routine on at least one image, following positive identification.

13. The system of claim 8 wherein said computer readable instructions are further configured to:
create an artificial intelligence quantum computer model of brain processes in a network user or users.

14. The system of claim 8 wherein said computer readable instructions are further configured to:
create the artificial intelligence computer model of the mental state-of-being during intelligence task processing, that could detect compromise in intelligence processing and seeks remedies by prompting suggestions during artificial intelligence word processing tasks, artificial intelligence video games, artificial intelligence operating systems, and changing autonomy-decision making level to upgrade or downgrade the level of the network user.

15. The system of claim 8 wherein said computer readable instructions are further configured to:
create the artificial intelligence computer model of the mental state-of-being during sensorimotor processing for purposes including telekinesis, telepsychic control, robotic telekinesis, human-brain telerobotic surgery, and during scanning of any part of the body with an ultrasound probe with the goal of automated scanning task.

16. The system of claim 8 wherein said computer readable instructions are further configured to:
create the storage of data in blockchain and integrate artificial intelligence techniques to mine data on mental state-of-being to implement medical expert knowledge base system, diagnose mental stress conditions, diagnose a state of depression, detect microembolic signals and predict future actions.

17. A system for securely recording and storing mental performance data across a network in a multi-dimensional distributed database, said method comprising the steps of generating a blockchain comprising linked data blocks, said blockchain being configured to determine the mental state-of-being of the network user said system comprising:
microprocessor functionally connected to the computer in a modern avionic system to determine mental state-of-being of the human subject by monitoring brain electrical potentials, cerebral blood flow, cerebral blood flow velocity, brain oxygen consumption or cerebral metabolism; said data is mined with artificial intelligence technologies to monitor the mental state-of being of the said human subject to determine the level of consciousness, attention, proficiency in task execution and regulate autonomy-decision making level between the human subject, avionic control computer and the land-based mission control center.

18. The system of claim 17, wherein a plurality of new blocks can be generated simultaneously from different nodes of the distributed network by adding new blocks to the consensus blockchain from the node sidechains, wherein the nodes function in an artificial intelligence neural network.

19. The system of claim 17, wherein each node forms a fork block in said slidechain using a different set of protocols for each node, said protocol could be used for detection of patterns for mental stress, attention deficit, and sleep.

20. The system of claim 17, wherein each node has a blockchain in said slidechain which contains different types of mental performance data, that could be mined using artificial intelligence technologies, for purposes of positive identification, validation of financial transactions, intellectual property exchange, mental stress and diagnoses of diseases.

* * * * *